United States Patent
Fairhurst et al.

(10) Patent No.: US 6,329,366 B1
(45) Date of Patent: Dec. 11, 2001

(54) PHARMACEUTICAL COMPOUNDS

(75) Inventors: John Fairhurst, Kings Worthy; Peter Thaddeus Gallagher, Yateley; Martin Victor Miles, Hampton, all of (GB)

(73) Assignee: Eli Lilly and Company Limited, Basingstoke (GB)

( * ) Notice: Subject to any disclaimer, the term of this patent is extended or adjusted under 35 U.S.C. 154(b) by 0 days.

(21) Appl. No.: 09/442,904

(22) Filed: Nov. 18, 1999

(30) Foreign Application Priority Data

Nov. 19, 1998 (GB) .................................... 9825413

(51) Int. Cl.⁷ .................... C07D 417/14; C07D 285/16; A61K 31/549; A61P 25/18; A61P 25/24

(52) U.S. Cl. .................... 514/222.8; 514/226.5; 514/259; 514/312; 514/318; 514/322; 514/323; 514/362; 514/372; 514/387; 514/414; 544/11; 544/49; 544/284; 544/286; 546/158; 546/198; 546/199; 546/201; 548/134; 548/207; 548/305.1; 548/455

(58) Field of Search ............... 514/222.8, 226.5, 514/259, 312, 318, 323, 321, 322, 362, 372, 387, 414; 544/49, 11, 284, 286; 546/158, 199, 201, 334, 198; 548/134, 207, 305.1, 455

(56) References Cited

U.S. PATENT DOCUMENTS 5,670,511    9/1997    Marz et al. .................... 514/290
5,929,072  * 7/1999    Fairhurst ...................... 514/222.8

FOREIGN PATENT DOCUMENTS

0897921 A1   2/1999   (EP) .
2093455 A    9/1982   (GB) .
WO 98/31686  7/1998   (WO) .
WO 99/58525  11/1999  (WO) .

OTHER PUBLICATIONS

Guillaume, J., et al., *Eur. J. of Med. Chem.*, 22:1, 33–43 (1987).
Chemical Abstract No. 103:37416, K. Freter, et al., Arzneim.–Forsch., 35 (1A), 272–276 (1985).
Guillaume, J., et al., *Eur. J. of Med. Chem.*, 22:1, 33–43 (1987).
Chemical Abstract No. 103:37416, K. Freter, et al., Arzneim.–Forsch., 35(1A), 272–276 (1985).

* cited by examiner

*Primary Examiner*—Mukund J. Shah
*Assistant Examiner*—Thomas McKenzie
(74) *Attorney, Agent, or Firm*—Manisha A. Desai

(57) ABSTRACT

A pharmaceutical compound of the formula

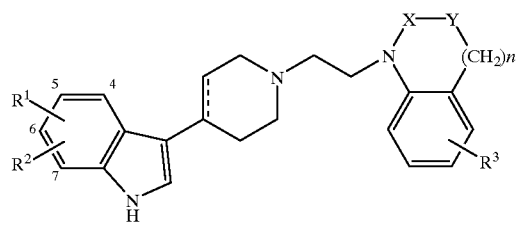

(I)

in which $R^1$ and $R^2$ are each hydrogen, halo, cyano or methyl, the dotted line represents an optional double bond,

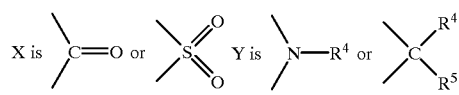

where $R^4$ and $R^5$ are each hydrogen, $C_{1-6}$ alkyl, cyclopropyl or cyclopropyl-$C_{1-6}$ alkyl, n is 0 or 1, and $R^3$ is —$SR^6$, —$SOR^6$, —$SO_2R^6$, —$COR^6$, —$CH_2OH$ or —$CONHR^7$, where $R^6$ is $C_{1-6}$ alkyl and $R^7$ is hydrogen or $C_{1-6}$ alkyl;

provided that when one of $R^1$ and $R^2$ is hydrogen and the other is fluoro,

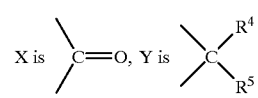

$R^4$ and $R^5$ are each hydrogen or $C_{1-6}$ alkyl, and n is 0, then $R^3$ is not —$COR^6$ or —$CONHR^7$;

and salts thereof.

10 Claims, No Drawings

PHARMACEUTICAL COMPOUNDS

This application claims the benefit of foreign priority from United Kingdom Application No. 0825413.9, filed Nov. 19, 1998.

This invention relates to pharmaceutical compounds and their use in the treatment of disorders of the central nervous system.

It is well known that compounds active at serotonin receptors have potential in the treatment of disorders of the central nervous system and, for example, certain halo-substituted indole compounds having serotonin antagonist properties are disclosed in WO 98/31686.

The compounds of the invention have the following formula:

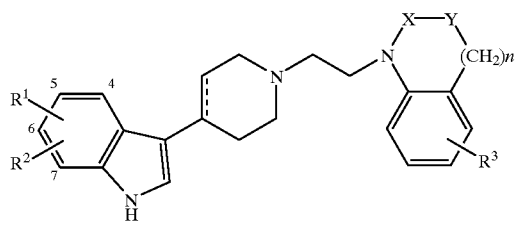

(I)

in which $R^1$ and $R^2$ are each hydrogen, halo, cyano or methyl, the dotted line represents an optional double bond,

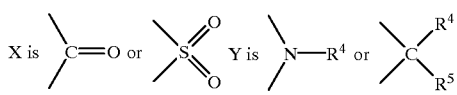

where $R^4$ and $R^5$ are each hydrogen, $C_{1-6}$ alkyl, cyclopropyl or cyclopropyl-$C_{1-6}$ alkyl, n is 0 or 1, and $R^3$ is —$SR^6$, —$SOR^6$, —$SO_2R^6$, —$COR^6$, —$CH_2OH$ or —$CONHR^7$, where $R^6$ is $C_{1-6}$ alkyl and $R^7$ is hydrogen or $C_{1-6}$ alkyl;

provided that when one of $R^1$ and $R^2$ is hydrogen and the other is fluoro,

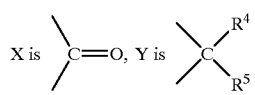

$R^4$ and $R^5$ are each hydrogen or $C_{1-6}$ alkyl, and n is 0, then $R^3$ is not —$COR^6$ or —$CONHR^7$;

and salts thereof.

The compounds of the invention and their pharmaceutically acceptable salts are indicated for use in the treatment of disorders of the central nervous system.

In the above formula (I), a halo atom is preferably chloro, bromo or fluoro, and is especially fluoro. A $C_{1-6}$ alkyl group can be methyl, ethyl, propyl, butyl or pentyl, and can be branched or unbranched including isopropyl and tert. butyl.

Preferred compounds are those which have one or more of the following features:

(i) $R^1$ and $R^2$ are each hydrogen or halo;
(ii) $R^1$ and $R^2$ are each hydrogen or fluoro;
(iii) $R^1$ is fluoro and $R^2$ is hydrogen;
(iv) $R^1$ is fluoro in the 6-position, and $R^2$ is hydrogen;
(v) the dotted line represents a double bond;
(vi)

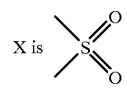

(vii)

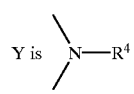

(viii) $R^4$ and $R^5$ are each hydrogen or $C_{1-6}$ alkyl;
(ix)

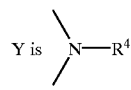

where $R^4$ is $C_{1-6}$ alkyl, especially isopropyl;

(x) n is 1;
(xi) n is 1 and $R^3$ is at the 6-position;
(xii) $R^3$ is —$SOR^6$, —$SO_2R^6$ or —$COR^6$;
(xiii) $R^6$ is methyl or ethyl, and especially methyl;
(xiv) $R^3$ is —$SOCH_3$ or —$SO_2CH_3$, at the 6-position.

A preferred group of compounds is of the following formula:

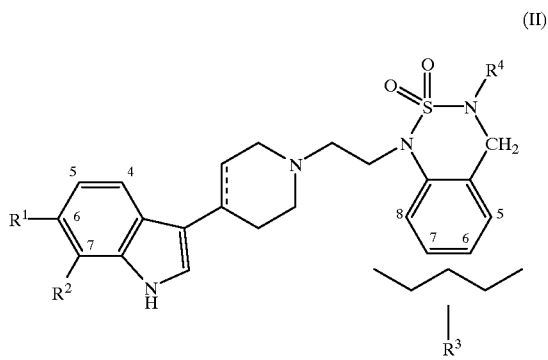

(II)

in which $R^1$ and $R^2$ are each hydrogen or fluoro, $R^3$ is at the 6- or 7- position and is —$SOR^6$, —$SO_2R^6$ or —$COR^6$, where $R^4$ and $R^6$ are each $C_{1-6}$ alkyl, especially methyl or ethyl.

Especially preferred are compounds of formula (II) in which $R^1$ is fluoro, $R^2$ is hydrogen, $R^3$ is at the 6-position, $R^4$ is $C_{1-6}$ alkyl, preferably isopropyl, $R^6$ is preferably methyl, and preferably the dotted bond represents a double bond.

Especially preferred compounds are of the formula:

(III)

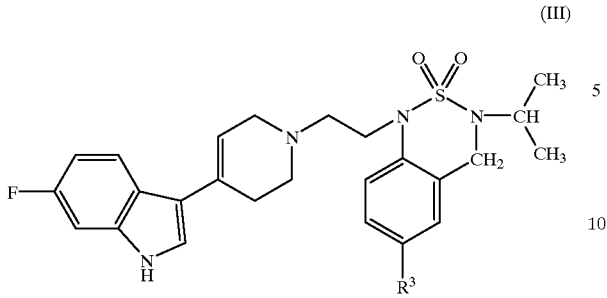

where R³ is —SOCH₃ or —SO₂CH₃, or a pharmaceutically acceptable salt thereof.

As indicated above, it is, of course, possible to prepare salts of the compound of the invention and such salts are included in the invention. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, pyruvic, lactobionic, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, naphthalene-2-sulphonic, bisethanesulphonic acid or methanesulphonic acid. A preferred salt is the tartrate.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

Some of the compounds of the invention contain one or more asymmetric carbon atoms which gives rise to isomers. Moreover, compounds which are substituted by a sulphinyl group (R³ is —SOR⁶) also exist in isomeric forms. These compounds are normally prepared as racemic mixtures and can conveniently be used as such, but individual isomers can be isolated by conventional techniques, if so desired. Such racemic mixtures and individual optical isomers form part of the present invention. It is preferred to use an enantiomerically pure form.

The invention also includes a process for producing a compound of formula (I) above, which comprises reacting a compound of the formula:

(IV)

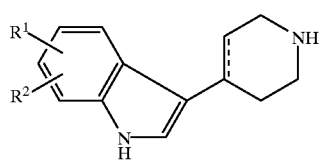

with a compound of the formula (V)

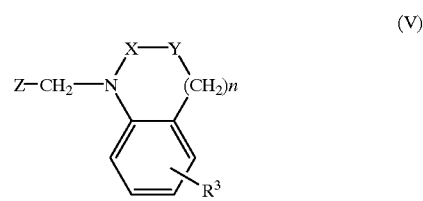

where n, R¹, R², R³, X and Y have the values given above, and (i) Z is —CH₂W, where W is a leaving group such as, for example, a halo atom or a mesylate or tosylate, or (ii) Z is —CHO.

The reaction is preferably carried out in a polar solvent such as, for example, acetonitrile or water, at a temperature of from 50° C. to 150° C., and in the presence of sodium iodide and a base such as, for example, sodium carbonate. When an aldehyde intermediate is employed, the reaction is one of reductive amination using, for example, sodium cyanoborohydride, borane in pyridine or triacetoxy borohydride in the presence of the compound of formula (IV).

The intermediate compounds of formula (IV) are known in the art, whereas compounds of formula (V), and their salts, in which n is 1, are novel. Compounds of formula (V) can be prepared by reacting an ethane derivative of the formula V—CH₂CH₂—W (VI), where V is halo, preferably bromo, with a compound of formula:

(VII)

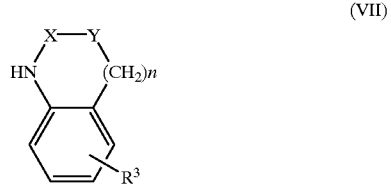

Preferred ethane derivatives of formula (VI) are dihaloethanes, for instance bromo chloroethane, and the reaction is preferably carried out in an organic solvent such as, for example, dimethyl formamide, with a strong base such as sodium hydride, at a temperature of from 0° C. to 100° C., for instance room temperature.

Aldehyde intermediates of formula (V) can be prepared from the appropriate alkene by oxidation employing, for example, ozone or osmium tetroxide.

Alternatively, compounds of formula (V) can be prepared by a synthetic route, such as the following:

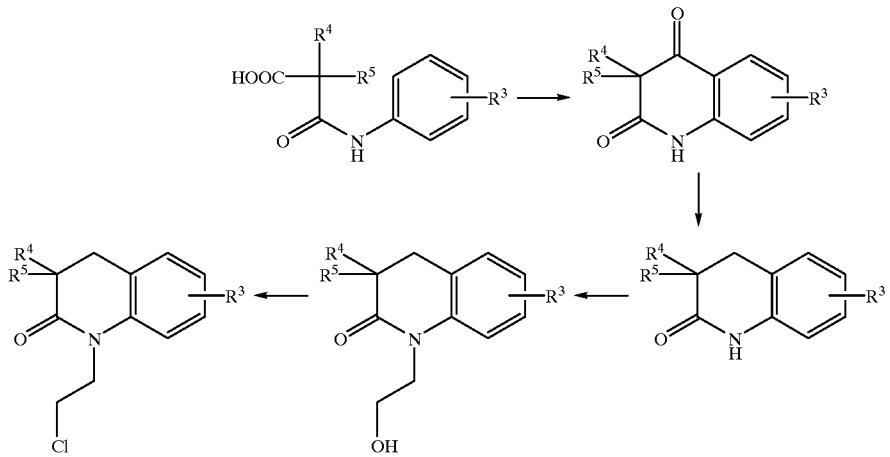

or by the following route:

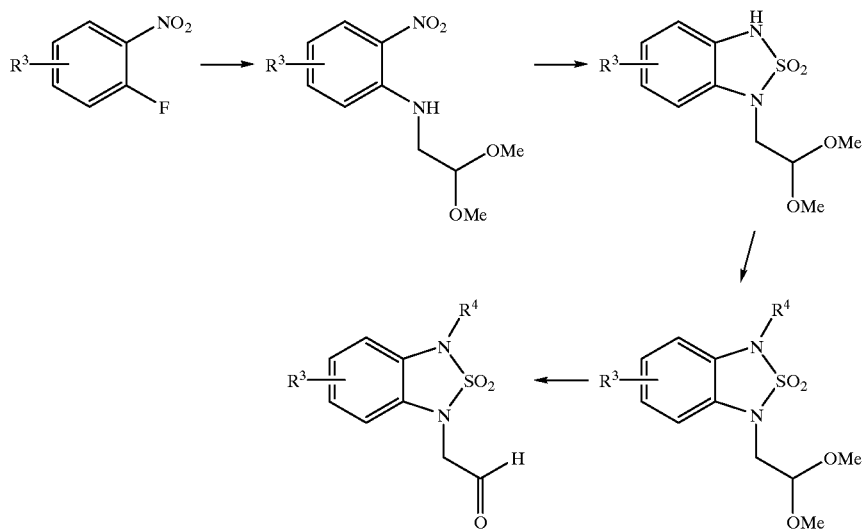

The intermediate compounds of formula (VII) are known in the literature, and they can readily be prepared by a variety of routes as, for example, in the case of compounds of formula (VII) having the following structure:

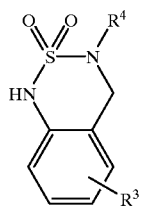

(VIII)

the principal route of synthesis is by means of a reaction between the appropriate sulfamoyl compound prepared from an aniline and sulfamoyl chloride and trioxan, in the presence of an acid, for example, an alkyl sulfonic acid:

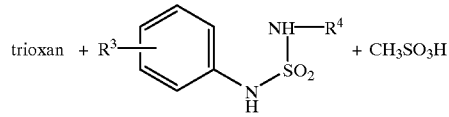

Alternatively, compounds of formula (VIII) can be synthesised by reaction of sulfamide with an amino benzylamine in pyridine or diglyme. The amino benzylamine can be prepared in three steps from the appropriate nitrobenzoic acid via amide formation and a two step reduction as, for example:

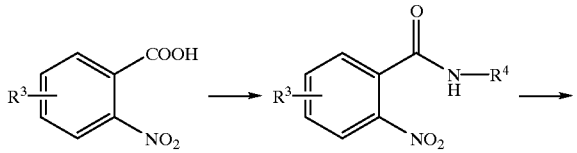

-continued

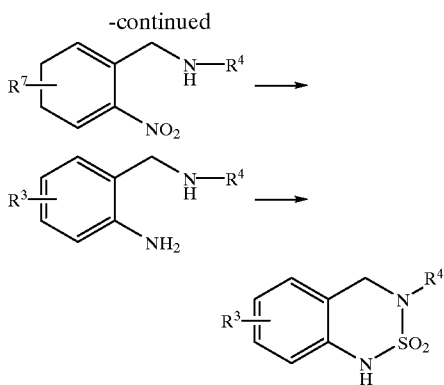

A further alternative route to compounds of formula (VIII) involves the use of an appropriate N-sulfamoyloxazolidinone of formula:

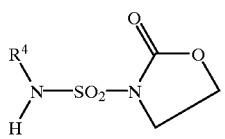

which can be readily prepared by reacting chlorosulfonyl-isocyanate and amine with chloro- or bromo-ethanol. The N-sulfamoyloxazolidinone is then reacted with an aniline of formula

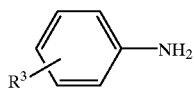

and the resulting sulfonyl urea reacted with trioxan, as described above, to give the compound of formula (VIII).

An alternative route to the compounds of the invention in which in formula (I) X is:

consists of an analogous, reverse, condensation of the two principal components of the molecule as, for example, by reacting a compound of the formula:

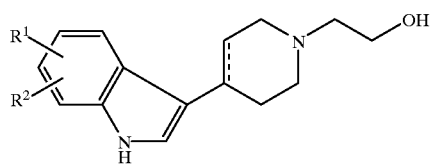

(IX)

with a compound of formula (VIII) above, employing the Mitsunobu reaction. The reaction is carried out in an organic solvent such as tetrahydrofuran or dimethyl formamide, at a temperature of, for example, 0° C. to 5° C. employing a dialkylazodicarboxylate and triphenylphosphine or tributylphosphine. Intermediate compounds of formula (IX) are novel and are included as part of the present invention.

It will be appreciated that in preparing compounds of formula (I) in which $R^3$ is —$SOR^6$ or —$SO_2R^6$, the appropriate intermediates as, for example, those of formula (VIII), can be prepared by oxidation of the —$SR^6$ substituted compound, by the use of metachloro perbenzoic acid or Oxone® or sodium perborate or osmium tetroxide/sodium periodate.

As mentioned above, the compounds of the invention and their pharmaceutically acceptable salts have useful central nervous system activity. They have been shown to increase release of tritiated-5HT from guinea pig cortical slices in a test with the following procedure.

Cortical slices from the brains of male guinea pigs were incubated with 50 nM [$^3$H]-5-HT for 30 minutes at 37° C. The slices were washed in basal buffer containing 1 μM paroxetine and then transferred to baskets. The baskets were used to transfer the tissue between the washing and release buffers, all of which contained 1 μM paroxetine.

In order to obtain a stable baseline release, the slices were incubated for 11 minutes in buffer and then transferred for 4 minutes to a second tube containing buffer. Following incubation they were again transferred, for a further 4 minutes, to a buffer in which NaCl had been substituted, on an equimolar basis, to give a KCl concentration of 30 mM (release sample). The tritium in the tissue samples and in the buffers from the three incubation periods was estimated by liquid scintillation spectroscopy. Test compound was present throughout the three incubation periods. The compounds of the invention enhanced release of 5-HT by greater than 35% at 1 μM concentration.

Compounds of the invention have also been demonstrated to be active at the serotonin, 5-HT2A, receptor. Their binding activity has been demonstrated in a test described by Nelson, D. L. et al, J. Pharmacol. Exp. Ther., 265, 1272–1279, in which the affinity of the compound for the human 2A receptor is measured by its ability to displace the ligand [$^3$H]-ketanserin. Compounds of the invention are also active serotonin reuptake inhibitors as measured by their displacement of [$^3$H]-paroxetine at the reuptake site, Neuropharmacology Vol. 32 No. 8, 1993, pages 737–743.

Because of their ability to enhance 5-HT release as well as selective affinity for 5-HT receptors, the compounds of the present invention are indicated for use in treating a variety of conditions such as depression, obesity, bulimia, alcoholism, pain, hypertension, ageing, memory loss, sexual dysfunction, anxiety, schizophrenia, gastrointestinal disorders, headache, cardiovascular disorders, smoking cessation, drug addiction, emesis, epilepsy, Alzheimer's and sleep disorders.

The compounds of the invention are effective over a wide dosage range, the actual dose administered being dependent on such factors as the particular compound being used, the condition being treated and the type and size of mammal being treated. However, the dosage required will normally fall within the range of 0.01 to 20 mg/kg per day, for example in the treatment of adult humans, dosages of from 0.1 to 100 mg per day may be used, preferably from 2 to 20 mg per day as, for example, for the preferred compounds of formula (II) and (III).

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt or ester thereof, associated with a pharmaceutically acceptable excipient. In making the compositions of the invention, the active ingredient will usually be mixed with a carrier, or diluted by a carrier, or enclosed within a carrier which may be in the form of a capsule, sachet, paper or other container. The excipient may be a solid, semi-solid or liquid material which acts as a vehicle, excipient or medium for the active ingredient. Some examples of suitable excipients are lactose, dextrose, sucrose, sorbitol, mannitol, starches, gum acacia, calcium phosphate, alginates, tragacanth, gelatin syrup, methyl cellulose, methyl- and propyl-hydroxybenzoate, talc, magnesium stearate or oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions or suspensions for parenteral use or as suppositories. Preferably the compositions are formulated in a dosage unit form, each dosage containing from 0.1 to 100 mg, more usually 2 to 20 mg, of the active ingredient.

The following Preparations and Examples illustrate routes to the synthesis of the compounds of the invention.

PREPARATIONS

1-Dimethylamino-2-(4-fluoro-2-nitro)phenylethene

A mixture of 4-fluoro-2-nitrotoluene (50 g, 0.32 mol), dimethylformamide dimethylacetal (76.77 g) and dimethylformamide (910 ml) were heated under reflux under nitrogen with stirring for 7 hr, cooled, allowed to stand for 16 hr, poured into ice-water (2 l), stirred for 15 mins and the resultant precipitate isolated by filtration, washed with water (500 ml), dried to give a red solid. (Org. Synth. (1985), 63, 214–25)

6-Fluoro-1H-indole

A 40 liter Cook hydrogenator was charged under a nitrogen atmosphere with 10% palladium on charcoal (9 g) suspended in toluene (400 ml). To this suspension was added 1-dimethylamino-2-(4-fluoro-2-nitro)phenylethene (137.2 g, 0.653 mol) in toluene (1.4 l) and the mixture hydrogenated at 80 psi for 3.5 hr. The suspension was then filtered through a celite pad, which was washed through with toluene (2×200 ml) and the filtrate and washings evaporated under reduced pressure to give a brown oil which crystallised on standing to a yellow brown solid 93.65 g. This solid was dissolved in ethyl acetate-hexane (7:3) and filtered through a pad of flash silica. The required fractions were collected and evaporated under reduced pressure to give a pale brown solid. (Org. Synth. (1985), 63, 214–25)

7-Fluoro-1H-indole

2-Fluoro-1-nitrobenzene (20.0 g, 0.142 mol) was dissolved in dry tetrahydrofuran (400 ml) and cooled to −50° C. Vinylmagnesium chloride (288 ml, 15% wt/vol) was added at −45° C. and stirred at this temperature for 1 hr. The reaction mixture was then poured onto saturated ammonium chloride (600 ml), separated and the aqueous layer extracted with diethyl ether (2×200 ml) then dried (MgSO$_4$), filtered and concentrated in vacuo to yield a dark oil which was purified by column chromatography on silica using toluene as mobile phase. Fractions concentrated to yield a crystalline solid. (Tetrahedron Lett. (1989), 30(16), 2129–32)

7-Fluoro-1H-indole (Alternative preparation)

To a stirred solution of boron trichloride in dichloromethane (1.0 M, 3.650 l, 3.65 mol) at −10° C. under nitrogen was added 2-fluoroaniline (387 g, 3.48 mol) and the temperature rose to 18° C. The mixture was stirred for 45 mins before chloroacetonitrile (300 g, 3.97 mol) followed by aluminium chloride (500 g, 3.75 mol) were added. 1,2-Dichloroethane (5.7 l) was then added, the mixture heated and the dichloromethane distilled from the reaction vessel. The dichloroethane solution was then heated at 78–80° C. for 18 hr. The reaction mixture was then cooled to 2° C. and hydrochloric acid (2.5M, 450 ml) was added slowly with a resultant exotherm. More hydrochloric acid (2.5M, 5.55 l) was added and then the mixture was warmed to reflux for 10 mins then cooled. The dichloroethane layer was separated and the aqueous layer extracted with dichloromethane (1 l) combined with the dichloroethane, washed with brine (2 l), dried (MgSO$_4$), filtered and the solvent evaporated in vacuo to give a solid 321.7 g. This solid was dissolved in a mixture of dioxan (10 l) and water (1 l) and treated under nitrogen with sodium borohydride (73.0 g, 1.93 mol) then heated under reflux for 1 hour. More sodium borohydride (12 g) was added and the mixture heated for a further 3 hr, cooled to 45° C. and the solvent removed in vacuo. The residue was partitioned between dichloromethane (2 l) and water (2 l). The organic layer was separated, dried (MgSO$_4$), filtered and evaporated in vacuo to give an oil which was further purified by filtering through silica.

Similarly prepared were:

6,7-Difluoro-1H-indole

δ($^1$H NMR, CDCl$_3$, ppm): 6.50 (1H, m), 6.90 (1H, m), 7.30 (2H, m), 8.4 (1H, br).

6-Fluoro-7-methyl-1H-indole (J.Med.Chem., 1976 19(3) 391–5)

δ($^1$H NMR, CDCl$_3$, ppm): 2.4 (3H, s), 6.50 (1H,), 6.90 (1H, t), 7.20 (1H, m), 7.4 (1H, m), 8.0 (1H, s).

6-Fluoro-3-(1,2,3,6-tetrahydro-4-pyridinyl)-1H-indole (EP 722941)

Powdered potassium hydroxide (144.4 g) was added carefully to a mechanically stirred mixture of 6-fluoroindole (49.23 g, 0.364 mol) and 4-piperidone monohydrate (111.93 g, 0.728 mol) in methanol (1500 ml). The mixture was then heated under reflux under nitrogen for 18 hr and then more potassium hydroxide (40 g) was added and the reaction mixture heated under reflux for a further 4 hr. The reaction mixture was allowed to cool to room temperature and poured onto ice-water (3 l) and stirred for 1 hr and the precipitated solid isolated by filtration and dried at 50° C. in vacuo to give a solid. (WO 9747302).

Similarly prepared were

5-Fluoro-3-(1,2,3,6-tetrahydro-4-pyridinyl)-1H-indole (J.Med.Chem., 1993 36(9) 1194).

6,7-Difluoro-3-(1,2,3,6-tetrahydro-4-pyridinyl)-1H-indole

δ($^1$H NMR, MeOD, ppm): 2.5 (2H, m), 3.0 (2H, t), 3.50 (2H ), 6.20 (1H ), 6.90 (1H, m), 7.3 (1H, s), 7.50 (1H, m).

6-Fluoro-7-methyl-3-(1,2,3,6-tetrahydro-4-pyridinyl)-1H-indole

δ($^1$H NMR, DMSO, ppm): 2.4 (4H, br), 3.0 (2H, m), 3.50 (2H ), 6.20 (1H ), 6.90 (1H, t), 7.4 (1H, s), 7.60 (1H, m), 11.2 (1H, br).

3-(1,2,3,6-Tetrahydro-4-pyridinyl)-1H-indole (J.Med.Chem., 1992 35(26) 4813–22)

6-Chloro-3-(1,2,3,6-Tetrahydro-4-pyridinyl)-1H-indole (EP 722941)

7-Fluoro-3-(1,2,3,6-tetrahydro-4-pyridinyl)-1H-indole (WO 9747302)

6-Fluoro-3-(4-piperidinyl)-1H-indole

A mixture of platinum oxide (1.0 g) in ethanol (37.5 ml) and glacial acetic acid (12.5 ml) were mixed under nitrogen with 6-fluoro-3-(1,2,3,6-tetrahydro-4-pyridinyl)-1H-indole (20 g, 0.0926 mol) in ethanol (187.5 ml) and glacial acetic acid (62.5 ml). The reaction mixture was then hydrogenated at 60 psi until the reaction was complete by tlc. The catalyst was removed by fitration and the solvent evaporated in vacuo to give a yellow solid which was dried at 60° C. in vacuo (EP 722941).

Similarly prepared were
5-Fluoro-3-(4-piperidinyl)-1H-indole (EP 705600)
6,7-Difluoro-3-(4-piperidinyl)-1H-indole δ($^1$H NMR, MeOD, ppm): 1.6–1.8 (2H, m), 1.95–2.05 (2H, m), 2.70–3.00 (3H, m ), 3.00–3.20 (2H, d), 6.80 (1H, m), 7.0 (1H, s), 7.30 (1H, m).
6-Chloro-3-(4-piperidinyl)-1H-indole (WO 9747302). 3-(4-Piperidinyl)-1H-indole (Helv Chim Acta 1968 51(2) 260–264).
2-(4-(6-Fluoro-1H-indol-3-yl)-3,6-dihydro-1(2H)-pyridinyl)ethanol.

To a stirred solution of 6-fluoro-3-(1,2,3,6-tetrahydro-4-pyridinyl)-1H-indole (1.0 g, 0.00462 mol) and triethylamine (0.77 ml, 0.00555 mol) in DMF (60 ml), was added dropwise under nitrogen 2-bromoethanol (0.42 ml, 0.00555 mol) then allowed to stir at room temperature overnight. Workup involved addition of ethyl acetate (80 ml) and water (50 ml), the organic layer was washed with water (4×50 ml). The organic layer was dried (MgSO$_4$) and concentrated in vacuo to afford 2-(4-(6-fluoro-1H-indol-3-yl)-3,6-dihydro-1(2H)-pyridinyl)ethanol as a yellow solid 1.02 g.

δ($^1$H NMR, DMSO, ppm): 11.3 (1H, s), 8.0 (1H, q), 7.5 (1H, s), 7.3 (1H, q), 7.0 (1H, m), 6.3 (1H, m), 4.6 (1 H, s), 3.7 (2H, t), 3.5 (2H, m), 3.4 (2H, m) , 2.8 (2H, m) , 2.6 (2H, t).
(1-Methylethyl)sulfamic acid A 250 ml 3-necked round bottom flask equipped with a magnetic stirrer bar, pressure equalising dropping funnel, thermometer and nitrogen gas bleed was charged with nitromethane (75 ml) and fuming sulfuric acid (30 g, i.e. oleum 12–17%). The mixture was cooled to 0° C. using an external cardice (solid CO$_2$)/acetone bath. Then isopropyl isocyanate (25 g, 0.294 mol) was added dropwise to the mixture, stirred under nitrogen, keeping the temperature below 30° C. during the addition. The stirred suspension was then heated under reflux for 30 mins, then allowed to cool to room temperature and stirred overnight. Diethyl ether (100 ml) was added to the mixture, which was then filtered. The filter pad was washed with more ether (3×100 ml) and then dried in an air stream at room temperature to give a pale yellow crystalline solid, (1-methyl ethyl)sulfamic acid. (JOC 1976 41 (25) 4028-9)

Similarly prepared was ethylsulfamic acid (JOC 1976 41 (25) 4028-9)
(1-Methylethyl)sulfamoyl chloride A 500 ml 3-necked round bottom flask equipped with a water condenser, thermometer and magnetic stirrer bar was charged with (1-methyl ethyl)sulfamic acid (34.8 g, 0.25 mol), phosphorus pentachloride (52.06 g, 0.25 mol) and toluene (400 ml). The mixture was warmed under reflux for 1 hr, then cooled back down to room temperature. The solvent was removed in vacuo to give a pale brown oil which was then purified by distillation under reduced pressure (approximately 15 mm Hg and 110° C.) to give a clear, colourless liquid, (1-methyl ethyl)sulfamoyl chloride (JOC 1976 41 (25) 4028-9)

Similarly prepared was ethylsulfamoyl chloride (JOC 1976 41 (25) 4028-9).
1-(Ethylthio)-4-nitrobenzene (Precursors for the synthesis of N-(4-ethylsulfonylphenyl)-N'-(1-methylethyl)sulfamide.

Ethanethiol (6.11 ml, 0.082 mol) was added slowly to a suspension of sodium hydride (3.3 g, 60% dispersion) in dry dimethylformamide (225 ml) at room temperature under a nitrogen atmosphere. The reaction mixture was stirred for 15 min before the addition of 1-chloro-4-nitrobenzene (10 g, 0.063 mol) dissolved in dry dimethylformamide (25 ml). After addition, the resultant mixture was allowed to warm to 60° C. and was stirred for 24 hr. The mixture was then concentrated in vacuo to yield a yellow oil. Ice and water were added and a yellow solid was precipitated and filtered off. The solid was then dissolved in methanol (100 ml) and insoluble by-products were isolated by filtration. The filtrate was then concentrated in vacuo. The residue was dissolved in ethyl acetate (50 ml) and washed with water (2×50 ml). The organic layer was then dried (MgSO$_4$) and concentrated in vacuo to afford 1-(ethylthio)-4-nitrobenzene as a yellow solid. δ($^1$H NMR, DMSO, ppm): 1.15 (3H, t), 3.05 (2H, q) 7.45 (2H, d), 8.10 (2H, d)
1-(Ethylsulfonyl)-4-nitrobenzene 1-(Ethylthio)-4-nitrobenzene (9 g, 0.049 mol) was dissolved in chloroform (500 ml). 3-chloroperoxybenzoic acid (21.14 g, 0.123 mol) was then added to the solution. After stirring at room temperature for 2 hr, the reaction mixture was filtered through celite. The filtrate was then dried (MgSO$_4$) and concentrated in vacuo to yield 1-(ethylsulfonyl)-4-nitrobenzene. δ($^1$H NMR, DMSO, ppm): 1.15 (3H, t), 3.40 (2H, q), 8.10 (2H, d), 8.40 (2H, d).
4-(Ethylsulfonyl)benzene amine Tin (II) chloride dihydrate (51.89 g, 0.230 mol) was added to 1-(ethylsulfonyl)-4-nitrobenzene (10 g, 0.046 mol) in ethanol (250 ml) then heated under reflux for 16 h. The mixture was cooled to room temperature and treated with aqueous sodium hydroxide (2N, 100 ml). The product was then extracted into ethyl acetate (3×150 ml). The organic extracts were combined, dried (MgSO$_4$) and concentrated in vacuo. The residue was then purified by chromatography column over silica (50% ethyl acetate/50% petroleum ether) to afford 4-(ethylsulfonyl)-benzene amine. δ($^1$H NMR, DMSO, ppm): 1.00 (3H, t), 2.95 (2H, q), 5.95 (2H, s), 6.55 (2H, d), 7.35(2H, d).
5-Methylthio-2-nitrobenzoic acid.

5-Chloro-2-nitrobenzoic acid (25.2 g, 0.125 mol) was stirred in water. To this was added sufficient sodium hydroxide solution (2M, 42 ml, 0.084 mol) to dissolve the acid completely. A solution of sodium sulfide nonahydrate (33.0 g, 0.1375 mol) in water (75 ml) was added and the solution was stirred at 60° C. for 2.5 hr. This resultant red solution was added to a solution of sodium hydroxide (50% 10 ml, 0.125 mol) in water (15 ml), dimethyl sulfate (24 ml, 0.25 mol) was added and the solution heated under reflux for 1 hour. The solution was cooled and acidified with hydrochloric acid (5M, 32 ml, 0.16 mol). The precipitated yellow solid was filtered off, washed with water, dried at 60° C. under vacuum, mp 173° C. (lit. J. Heterocyclic Chemistry 1981 18 117). Mp 175–178° C.)
N-Cyclopropylmethyl-5-methythio-2-nitrobenzamide.

To a suspension of 5-methylthio-2-nitrobenzoic acid (13.84 g, 0.065 mol) in hexane (130 ml) was added thionyl chloride (35 ml, 0.1298 mol) and heated under reflux for 1 hour by which time the acid had dissolved. The resultant reaction mixture was decanted from a tar-like material which had precipitated from the reaction mixture and the hexane solution was then evaporated in vacuo to give a yellow crystalline acid chloride (14.59 g, 97%, Mp 72° C.) which was used without further purification. The acid chloride (14.59 g, 0.063 mol) was dissolved in THF (60 ml) and added dropwise to a solution of cyclopropylmethylamine (5.8 g, 0.066 mol) and triethylamine (9.3 ml, 0.066 mol) in THF (60 ml) with mechanical stirring and ice-bath cooling to maintain the reaction at below 10° C. After all the acid chloride had been added the reaction mixture was allowed to warm to room temperature and stirred for 1 hr. The reaction mixture was then partitioned between chloroform and water, the organic phase was washed with water, dried (MgSO$_4$), filtered and evaporated to dryness then triturated with diethyl ether to give a yellow crystalline solid which was dried in vacuo at 50° C. to give N-cyclopropylmethyl-5-methythio-2-nitrobenzamide. Mp 134° C.

2-Amino-N-cyclopropylmethyl-5-methylthiobenzamide.

N-Cyclopropylmethyl-5-methythio-2-nitrobenzamide (15.08 g, 0.057 mol) was suspended together with Raney® Nickel (3.4 g) in methanol (250 ml) and hydrogenated at 60 psi and room temperature for 24 hr. The Raney® Nickel was then isolated by filtration through Celite®, the filtrate evaporated to dryness and the residue triturated with diethyl ether to give 2-amino-N-cyclopropylmethyl-5-methylthiobenzamide as a cream solid. Mp 124° C.

N-(1-methylethyl)-4-methylthio-2-nitrobenzamide.

A solution of 4-methylthio-2-nitrobenzoic acid (3.07 g, 0.01439 mol) [Lit. Ref. DE 2421541], isopropylamine (1.47 ml, 0.01728 mol) and pyridine (100 ml) was cooled in an ice bath. Silicon tetrachloride (2.01 ml, 0.01728 mol) was added dropwise under nitrogen over 15 mins. After stirring at room temperature for 2 hr the solution was refluxed for 7 hr, then allowed to cool to room temperature. The solution was added to water and concentrated in vacuo. The precipitate was dissolved in dichloromethane and washed twice with 1N hydrochloric acid (150 ml), dried and concentrated in vacuo to afford 2.82 g of amorphous yellow solid. $\delta$($^1$H NMR, CDCl$_3$, ppm): 1.10 (6H, d), 2.50 (3H, s), 4.2 (1H, m), 5.50 (1H, s), 7.35 (2H, m), 7.75 (1H, s).

N-[1-(2,2-Dimethoxyethyl)]-4-methylsulphonyl-2-nitroaniline

To a stirred solution of 2-fluoro-5-methylsulphonyl-1-nitrobenzene (3.75 g, 0.01711 mol) and sodium bicarbonate (1.58 g, 0.01882 mol) in DMF (80 ml) was added amino acetaldehyde dimethyl acetal (1.85 ml, 0.01711 mol). The solution was allowed to stir at room temperature for 30 mins. After the addition of water (130 ml) the product was extracted with ethyl acetate (3×75 ml) and the organic fractions collected and washed with water (3×75 ml). The organic fractions were dried (MgSO$_4$), filtered and concentrated in vacuo to afford an amorphous yellow solid.

$\delta$($^1$H NMR, CDCl$_3$, ppm): 3.00 (3H, s), 3.35 (2H, d), 3.45 (6H, s), 4.60 (1H, t), 6.7 (1H, d), 7.20 (1H, d), 7.40 (1H, dd).

N-(4-Methylthiophenyl)-2,2-dimethylmalonamic acid

Thionyl chloride (8.15 g, 5 ml, 0.069 mol) was added to a stirred solution of 2,2-dimethylmalonic acid (7.26 g, 0.055 mol) in dry THF (55 ml). The mixture was heated under reflux for 3 hr. The reaction mixture was cooled to room temperature and 4-methylthioaniline (15.3 g, 0.11 mol) in THF (30 ml) was then added dropwise over 30 mins to the solution. The mixture was stirred at room temperature for 2 hr. The reaction mixture was then concentrated in vacuo and then treated with hydrochloric acid (2N, 100 ml). The product was extracted with ethyl acetate (2×100 ml). The organic extracts were combined, then washed with water (100 ml) and saturated sodium hydrogen carbonate solution (5×80 ml). The organic layer was then acidified with hydrochloric acid (5N, 250 ml) and the resultant white crystalline precipitate was collected by filtration to afford N-(4-methylthiophenyl)-2,2-dimethylmalonamic acid. mp 130–132° C.

N-(4-Ethylsulfonylphenyl)-N'-(1-methylethyl)sulfamide (1-Methylethyl)sulfamoyl chloride (6.63 g, 0.034 mol) was added dropwise to a solution of 4-(ethylsulfonyl) benzene amine (6 g, 0.032 mol) and triethylamine (4.87 ml, 0.035 mol) in dry dichloromethane (100 ml) at 0° C. under a nitrogen atmosphere. After addition, the resultant mixture was allowed to warm to room temperature and was stirred for 6 hr. The reaction mixture was then washed with water (2×50 ml). The organic extracts were combined, dried (MgSO$_4$) and concentrated in vacuo to yield N-(4-ethylsulfonylphenyl)-N'-(1-methylethyl)sulfamide as a white solid. $\delta$($^1$H NMR, DMSO, ppm): 1.05 (6H, d), 1.10 (3H, t), 3.25 (2H, q), 3.40 (1H, m), 7.40 (2H, d), 7.80 (3H, m).

Similarly prepared were

N-(4-Methylthiophenyl)-N'-(1-methylethyl)sulfamide (Prepared from 4-(methylthio)benzene amine).

$\delta$($^1$H NMR, DMSO, ppm) 0.8 (6H, d), 2.3 (3H, s), 3.2 (1H, m), 3.35 (1H, s), 6.9–7.1 (4H, m), 9.5 (1H, s) . M.P. 65–68° C.

N-(4-Acetylphenyl)-N'-(1-methylethyl)sulfamide (Prepared from 4-aminoacetophenone)

$\delta$($^1$H NMR, CDCl$_3$, ppm): 1.1 (6H, d), 2.5 (3H, s), 3.5 (1H, m), 4.4 (1H, d), 6.80 (1H, s), 7.10 (2H, d), 7.90 (2H, d).

Ethyl 4-(1-methylethylsulfamoylamino)benzoate (Prepared from ethyl 4-aminobenzoate) Mp 146° C.

3,4-Dihydro-6-(ethylsulfonyl)-3-(1-methylethyl)-1H-2,1,3-benzothiadiazine-2,2-dioxide N-(4-Ethylsulfonylphenyl)-N'-(1-methylethyl)sulfamide (5 g, 0.016 mol) was dissolved in dry dichloromethane (150 ml) and methanesulphonic acid (18.87 ml, 0.303 mol). The solution was cooled at 0° C. before the addition of trioxan (0.480 g, 0.005 mol) in dichloromethane (15 ml). After stirring at 0° C. for 1 hr, the reaction mixture was poured onto ice-water (250 ml), the layers separated, dried (MgSO$_4$) and concentrated in vacuo to yield 3,4-dihydro-6-(ethylsulfonyl)-3-(1-methylethyl)-1H-2,1,3-benzothiadiazine-2,2-dioxide as a white solid. $\delta$($^1$H NMR, DMSO, ppm): 1.10 (9H, m), 3.30 (2H, q), 4.10 (1H, m), 4.80 (2H, s), 6.95 (1H, d), 7.75 (1H, dd), 7.80 (1H, d).

Prepared similarly were

Ethyl 3,4-dihydro-2,2-dioxo-3-(1-methylethyl)-1H-2,1,3-benzothiadiazine-6-carboxylate (Prepared from ethyl 4-(1-methylethylsulfamoylamino)benzoate) Mp 156° C.

6-Acetyl-3,4-dihydro-3-(1-methylethyl)-1H-2,1,3-benzothiadiazine-2,2-dioxide (Prepared from N-(4-acetylphenyl)-N'-(1-methylethyl)sulfamide)

$\delta$($^1$H NMR, CDCl$_3$, ppm): 1.0 (6H, d), 2.40 (3H, s), 4.00 (1H, m), 4.5 (2H, s) 6.55 (1H, d), 6.90 (1H, s), 7.60 (2H, m).

3,4-Dihydro-3-(1-methylethyl)-6-methylthio-1H-2,1,3-benzothiadiazine-2,2-dioxide (Prepared from N-(4-methylthiophenyl)-N'-(1-methylethyl) sulfamide.

$\delta$($^1$H NMR, DMSO, ppm): 0.9 (6H, d), 2.3 (3H, s), 3.9 (1H, m), 4.5 (2H, s), 6.6 (1H, d), 7.0 (2H, m), 10.1 (1H, s).

3,4-Dihydro-3-(1-methylethyl)-6-(methylsulfonyl)-1H-2,1,3-benzothiadiazine-2,2-dioxide A solution of OXONE® (potassium peroxymonosulfate) (5.65 g, 0.0092 mol) in water was added to a solution of 3,4-dihydro-3-(1-methylethyl)-6-(methylthio)-1H-2,1,3-benzothiadiazine-2,2-dioxide (1 g, 0.0037 mol) in acetone/water (25 ml/2.5 ml) stirring at room temperature. After 30 mins, water (25 ml) and ethyl acetate (50 ml) were added to the mixture. The two layers were separated and the organic layer was then dried (MgSO$_4$) and concentrated in vacuo to afford 3,4-dihydro-3-(1-methylethyl)-6-(methylsulfonyl)-1H-2,1,3-benzothiadiazine-2,2-dioxide as a pale yellow solid. $\delta$($^1$H NMR, CDCl$_3$, 300 MHz, ppm): 1.0 (3H, d), 2.9 (3H, s), 4.1 (1H, m), 4.6 (2H, s), 6.8 (1H, d), 7.6 (2H, m), 9.9 (1H, s).

3-Cyclopropylmethyl-6-methylthio-3,4-dihydro-1H-2,1,3-benzothiadiazine-2,2-dioxide.

2-Amino-N-cyclopropylmethyl-5-methylthiobenzamide (10.96 g, 0.0464 mol) was dissolved in dry toluene (175 ml)

in a 3 necked round bottomed flask equipped with a mechanical stirrer and a pressure equalising dropping funnel and cooled to 0° C. in an ice-water cooling bath. The pressure equalising dropping funnel was charged with toluene (45 ml) and sodium bis(2-methoxyethoxy)aluminium hydride (65 wt % in toluene, 45 ml, 0.1398 mol) and added dropwise to the reaction mixture. The reaction mixture was then warmed to room temperature, heated under reflux during 5 hr, and then cooled and poured into ice-water. The resulting two phase mixture was filtered through a celite pad to remove alumina. The aqueous phase was further extracted with toluene, the combined toluene extract was washed with water, brine, then dried ($MgSO_4$), filtered and the filtrate evaporated to an oily residue, which was dissolved in diethyl ether and extracted (3x) with hydrochloric acid (2M). The combined acidic extracts were washed with diethyl ether and then made basic with sodium hydroxide solution (2M) in the presence of diethyl ether. The ether layer was then separated washed with water, brine, dried ($MgSO_4$), filtered and evaporated to dryness to give an oil (9.17 g, 0.0412 mol) which was dissolved in diglyme (34 ml) and added to a magnetically stirred hot solution of sulphamide (4.7 g, 0.0474 mol) in diglyme (24 ml). The solution was stirred in an oil bath at 155–160° C. for 3 hr. The cooled solution was poured into water, the pH was adjusted to pH1 with 2M hydrochloric acid. The mixture was then triturated with ethyl acetate (2x). The combined organic phase was washed with water (2x), brine, 0.1 m hydrochloric acid and water again, dried over magnesium sulphate, filtered and the solvent removed to give an oil. This was chromatographed on flash silica (eluent ethyl acetate/hexane, 1:3) to give a waxy solid. Mp ~97° C.

3,4-Dihydro-3-(1-methylethyl)-7-(methylsulfonyl)-1H-2,1,3-benzothiadiazine-2,2-dioxide.

N-(1-Methylethyl)-4-methylthio-2-nitrobenzamide (2.76 g, 0.01085 mol) and tin (II) chloride (7.35 g, 0.03256 mol) in EtOH (150 ml) were stirred at reflux under nitrogen for 4 hr. The reaction was concentrated in vacuo and to the pale yellow oil was added water (100 ml) and 50% NaOH (20 ml). The solution was extracted twice with ethyl acetate (150 ml), dried over $MgSO_4$ and concentrated in vacuo. Column chromatography (eluent 50% ethyl acetate/hexane) afforded 1.84 g of white amorphous solid (76% yield). This solid (1.53 g, 0.00682mol) in dry THF (25 ml) was added to a suspension of lithium aluminium hydride (0.78 g, 0.02046 mol) in dry THF (75 ml) under nitrogen at 0° C. This solution was heated at reflux with stirring for 24 hr. The reaction was allowed to cool and 50% NaOH was added dropwise with stirring and cooling to the solution until the effervescence ceased. The reaction was filtered through celite and concentrated in vacuo. Column chromatography afforded a pale yellow crystalline solid (0.90 g, 63% yield). This solid (0.90 g, 0.00428 mol) in pyridine (25 ml) was then added to a stirred solution of sulfamide (0.45 g, 0.00471 mol) in pyridine (75 ml) held at reflux. After heating under reflux for 15 hr the solution was concentrated in vacuo and to the oil was added ethyl acetate (100 ml). After washing twice with water (50 ml) and 2N HCl (50 ml) the solution was dried over $MgSO_4$ and concentrated in vacuo to afford 3,4-dihydro-3-(1-methylethyl)-7-(methylthio)-1H-2,1,3-benzothiadiazine-2,2-dioxide as a pink amorphous solid.

δ($^1$H NMR, $CDCl_3$, ppm): 1.10 (6H, d), 2.50 (3H, s), 4.10 (1H, m), 4.60 (2H, s), 6.50 (1H, d), 6.95 (1H, dd), 7.00 (1H, d).

3,4-Dihydro-6-hydroxymethyl-3-(1-methylethyl)-1H-2,1,3-benzothiadiazine-2,2-dioxide.

Lithium aluminium hydride (0.4 g, 0.00105 mol) was added portionwise to a suspension of methyl 3,4-dihydro-3-(1-methylethyl)-1H-2,1,3-benzothiadiazine-2,2-dioxide-6-carboxylate (2.5 g, 0.0087 mol.) in THF (30 ml) at 0° C., under argon. The reaction was then warmed to room temperature for 15 hr, cooled to 0° C. and treated with water (9 ml) followed by 15% aqueous sodium hydroxide solution (9 ml), and then water (27 ml). After stirring for 1 hr the mixture is filtered through celite, the celite washed several times with 15% aqueous sodium hydroxide solution. The aqueous phase was adjusted to pH 4 with hydrochloric acid (3M), and extracted with dichloromethane, the dichloromethane extracts dried ($Na_2SO_4$) and evaporated to dryness yielding 3,4-dihydro-6-hydroxymethyl-3-(1-methylethyl)-1H-2,1,3-benzothiadiazine-2,2-dioxide.
$^1$H-NMR, $CDCl_3$, 300 Mz, δ: 7.13–7.09 (2H, m), 6.86 (NH, s), 6.60 (1H, d), 4.59 (4H, s), 4.14 (1H, m), 1.10 (6H, d).

6-t-Butyldimethylsiloxymethyl-3,4-dihydro-3-(1-methylethyl)-1H-2,1,3-benzothiadiazine-2,2-dioxide.

A suspension of 3,4-dihydro-6-hydroxymethyl-3-(1-methylethyl)-1H-2,1,3-benzothiadiazine-2,2-dioxide (2.2 g, 0.0087 mol) and imidazole (0.680 g, 0.0099 mol) in DMF (13 ml) was treated at 0° C., under argon with a solution of t-butyldimethylsilyl chloride (1.5 g, 0.0099 mol) in DMF (5 ml). After the addition, the reaction was stirred at room temperature for 3 hr. The reaction mixture was then poured over water and extracted with diethyl ether (3x). The organic phase was washed with water, dried ($Na_2SO_4$) and evaporated to dryness to yield a solid (3.2 g) which was triturated with hexane and then isolated by filtration to give 6-t-butyldimethylsiloxymethyl-3,4-dihydro-3-(1-methylethyl)-1H-2,1,3-benzothiadiazine-2,2-dioxide as a white solid.
$^1$H-NMR ($CDCl_3$, 300 Mz), δ: 7.14-7.02 (2H, m,), 6.62 (1H, d), 6.36 (NH, s), 4.64 (2H, s), 4.58 (2H, s), 4.16 (1H, m), 1.11 (6H, d), 0.90 (9H, s), 0.07 (6H, s).

3,3-Dimethyl-6-methylthio-2,4(1H,3H)-quinolinedione

Phosphorus pentoxide (4.49 g, 0.032 mol) was added to a stirred solution of N-(4-methylthiophenyl)-2,2-dimethylmalonamic acid (5.0 g, 0.020 mol) in methanesulfonic acid (35 ml). The reaction mixture was warmed to 70° C. and stirred for 90 mins. The product mixture was then cooled to room temperature and poured over ice. The product was extracted with ethyl acetate (2x200 ml). The organic extracts were combined, washed with water (200 ml), saturated sodium hydrogen carbonate solution (200 ml), dried ($MgSO_4$) and concentrated in vacuo to give 3,3-dimethyl-6-methylthio-2,4(1H,3H)-quinolinedione as a yellow solid. Mp 152° C.

3,4-Dihydro-3,3-dimethyl-6-methylthio-2(1H)-quinolinone

Triethylsilane (34.75 ml, 49.1 g, 0.042 mol) was added dropwise to a stirred solution of 3,3-dimethyl-6-methylthio-2,4(1H,3H)-quinolinedione (12.79 g, 0.054 mol) in trifluoroacetic acid (520 ml) under nitrogen at 60° C. The reaction was then allowed to cool slowly to room temperature and was stirred for 16 hr. The solvent was then evaporated in vacuo to afford a yellow residue. The residue was then poured into saturated potassium carbonate solution (200 ml). The product was extracted with ethyl acetate (3x150 ml) The organic extracts were combined, washed with water (200 ml), dried and concentrated in vacuo to afford 3,4-dihydro-3,3-dimethyl-6-methylthio-2(1H)-quinolinone as a yellow solid. Mp 154° C.

5-Bromo-3,3-dimethyl-1,3-dihydro-2H-indol-2-one.

3,3-Dimethyl-1,3-dihydro-2H-indol-2-one (1.12 g, 0.00695 mol) was dissolved in chloroform and stirred at room temperature under nitrogen. Bromine (1.12 g) was added and the mixture was heated under reflux until HBr evolution ceased and the bromine colour was discharged from the solution. The solution was washed with sodium metabisulphite solution and sodium hydrogen carbonate solution, dried (MgSO$_4$), filtered and concentrated to dry under reduced pressure to give 5-bromo-3,3-dimethyl-1,3-dihydro-2H-indol-2-one as a yellow solid. $^1$H NMR (CDCl$_3$) 1.39 (6H s), 6.8 (1H d), 7.3 (2H m), 7.9 (1H broad).

1,3-Dihydro-1-[1-(2,2-dimethoxyethyl)]-5-methylsulphonyl-2,1,3-benzothiadiazole-2,2-dioxide N-[1-(2,2-Dimethoxyethyl)]-4-methylsulphonyl-2-nitroaniline (4.68 g, 0.01538 mol) was dissolved in methanol (100 ml) containing 10% palladium on charcoal (0.55 g) and hydrogenated at 70 psi for 20 mins. After removal of the catalyst, the solution was concentrated in vacuo to afford a pale pink amorphous solid (4.22 g, 100% yield). This compound (3.96 g, 0.01443 mol) in pyridine (50 ml) was added slowly to a refluxing solution of sulphamide (1.53 g) in pyridine (200 ml) and the reaction heated for a further 15 hr. The reaction was cooled to room temperature, water added (100 ml) and the product extracted with ethyl acetate (3×70 ml). The organic fractions were collected, washed with water (150 ml) and 2N hydrochloric acid solution (2×100 ml). The organic layer was dried (MgSO$_4$) filtered and concentrated in vacuo to afford the product.

δ($^1$H NMR, CDCl$_3$, ppm): 3.00 (3H, s), 3.45 (6H, s), 3.80 (2H, d), 4.70 (1H, t), 7.1 (1H, d), 7.40 (1H, d), 7.60 (1H, dd).

1,3-Dihydro-1-[1-(2,2-dimethoxyethyl)]-3-methyl-5-methylsulphonyl-2,1,3-benzothiadiazole-2,2-dioxide To a stirred solution of 1,3-dihydro-1-[1-(2,2-dimethoxyethyl)]-5-methylsulphonyl-2,1,3-benzothiadiazole-2,2-dioxide (2.82 g, 0.00838 mol) in DMF (100 ml) was added portionwise sodium hydride (0.67 g, 0.01677 mol; 60% dispersion in oil) and allowed to stir at room temperature for 3 hr. To this solution was added iodomethane (0.63 ml, 0.01006 mol) and the resultant mixture was heated at 60° C. overnight. The reaction was allowed to cool to room temperature and water (150 ml) added. The product was extracted with ethyl acetate (2×100 ml) and the combined organic fractions washed with saturated sodium hydrogen carbonate solution (2×100 ml) and water (2×100 ml). The organic extracts were dried (MgSO$_4$) filtered and concentrated in vacuo to afford title product after chromatography.

δ($^1$H NMR, CDCl$_3$, ppm): 3.00 (3H, s), 3.40 (3H, s), 3.50 (6H, s), 3.90 (2H, d), 4.7 (1H, t), 7.10 (1H, d), 7.30 (1H, s) 7.6 (1H, dd).

3,4-Dihydro-3,3-dimethyl-1-(2-hydroxyethyl)-6-methylthio-2(1H)-quinolinone.

Sodium hydride (0.558 g at 60% dispersion, 0.015 mol) was added in portions to a stirred solution of 3,4-dihydro-3,3-dimethyl-6-methylthio-2(1H)-quinolinone (2.5 g, 0.0113 mol) in dry DMF (12 ml) at 0° C. under nitrogen. The mixture was then allowed to warm to room temperature and stirred for 40 mins before 2-(2-chloroethoxy)-tetrahydropyran (2.5 ml, 2.79 g, 0.017 mol) was added. After addition, the resultant mixture was warmed to 70° C. and was stirred for 12 hr. The mixture was then poured into diethyl ether (100 ml), washed with hydrochloric acid (1M, 3×50 ml), washed with water, dried (MgSO$_4$) and the filtrate evaporated in vacuo to give an oil (5.369 g). The residue was immediately dissolved in methanol (30 ml) and treated with p-toluenesulfonic acid (0.25 g) and stirred at room temperature for 2 hr. The methanol was then evaporated in vacuo and the residue washed with sodium hydrogen carbonate solution, dried (MgSO$_4$), filtered and the solvent evaporated in vacuo to give 3,4-dihydro-3,3-dimethyl-1-(2-hydroxyethyl)-6-methylthio-2(1H)-quinolinone. δ($^1$H NMR, CDCl$_3$, ppm): 7.3 (1H, dd), 7.2 (1H, d), 7.1 (1H, d), 4.2 (2H, t), 4.0 (2H, m), 2.9 (2H, s), 2.6 (3H, s), 1.8 (1H, OH), 1.4 (6H, s).

3,4-Dihydro-3-(1-methylethyl)-6-methylthio-1-(prop-2-en-1-yl)-1H-2,1,3-benzothiadiazine-2,2-dioxide.

3,4-Dihydro-3-(1-methylethyl)-6-methylthio-1H-2,1,3-benzothiadiazine-2,2-dioxide (10 g, 0.0367 mol) was added to a suspension of sodium hydride (1.61 g, 60% dispersion) in dry dimethylformamide (200 ml) at room temperature under a nitrogen atmosphere. The pale grey suspension was stirred for ten mins, and then allyl bromide (3.49 ml, 0.0404 mol) was added in one portion. The reaction mixture was stirred at 80° C. for 3 hr. The mixture was then concentrated in vacuo to yield a brown residue. The residue was dissolved in ethyl acetate (50 ml) and washed with water (2×50 ml). The organic layer was then dried (MgSO$_4$) and concentrated in vacuo to afford 3,4-dihydro-3-(1-methylethyl)-6-methylthio-1-(prop-2-en-1-yl)-1H-2,1,3-benzothiadiazine-2,2-dioxide. δ($^1$H NMR, DMSO, ppm): 1.1 (6H, d), 2.5 (3H, s), 4.1 (1H, m), 4.5 (2H, d), 4.7 (2H, s), 5.3 (1H, dd), 5.4 (1H, dd), 6.0 (1H, m), 7.0 (1H, d), 7.3 (2H, m).

[3,4-Dihydro-2,2-dioxido-3-(1-methylethyl)-6-methylsulfonyl-1H-2,1,3-benzothiadiazin-1-yl]ethanal.

3,4-Dihydro-3-(1-methylethyl)-6-methylthio-1-(prop-2-en-1-yl)-1H-2,1,3-benzothiadiazine-2,2-dioxide (10 g, 0.032 mol) was dissolved in dioxan (100 ml) and water (20 ml). Osmium tetroxide (2 crystals) was added to the solution and the mixture was stirred for five mins at room temperature, before the addition of sodium periodate (34.28 g, 0.160 mol) dissolved in water (25 ml). After stirring at ambient temperature for 14 hr, the reaction mixture was filtered through Celite®. The filtrate was then concentrated in vacuo to yield an oil. The oil was dissolved in ethyl acetate (100 ml) and washed with water (2×50 ml). The organic layer was then dried and concentrated in vacuo to afford [3,4-dihydro-2,2-dioxide-3-(1-methylethyl)-6-methylsulfonyl-1H-2,1,3-benzothiadiazin-1-yl]ethanal as a yellow solid. δ($^1$H NMR, DMSO, ppm): 1.1 (6H, d), 3.2 (3H, s), 4.0 (1H, m), 4.8 (2H, s), 4.9 (2H, s), 7.0 (1H, d), 7.7 (1H, dd), 7.8 (1H, d), 9.6 (1H, s).

[1,3-Dihydro-2,2-dioxido-3-methyl-5-methylsulphonyl-2,1,3-benzothiadiazol-1-yl]ethanal 1,3-Dihydro-1-[1-(2,2-dimethoxyethyl)]-3-methyl-5-methylsulphonyl-2,1,3-benzothiadiazole-2,2-dioxide (1.4 g, 0.004 mol) and 20% HCl (20 ml) in acetone (15 ml) were allowed to stir at room temperature overnight. Further 20% HCl (10 ml) was added and the solution stirred for 6 hr. The reaction was neutralised with saturated sodium hydrogen carbonate solution and the product extracted with ethyl acetate (3×100 ml). The organic fractions were dried (MgSO$_4$) and concentrated in vacuo to afford the product.

δ($^1$H NMR, CDCl$_3$, ppm): 3.00 (3H, s), 3.40 (3H, s), 4.60 (2H, s), 6.70 (1H, d), 7.35 (1H, d) 7.6 (1H, dd), 9.75 (1H, s)

1-(2-Chloroethyl)-3,4-dihydro-3-(1-methylethyl)-6-methylthio-1H-2,1,3-benzothiadiazine-2,2-dioxide.

To a 250 ml 3 necked flask equipped thermometer, pressure equalised dropping funnel, nitrogen bubbler and magnetic stirrer bar was added 60% sodium hydride (1.77 g, 1.062 g, 0.04425 mol,) hexane washed, to dry DMF (75 ml). To this stirred suspension was added dropwise a solution of 3,4-dihydro-3-(1-methylethyl)-6-methylthio-1H-2,1,3-benzothiadiazine-2,2-dioxide (10.0 g, 0.0368 mol) in dry DMF (75 ml) (slight exotherm). The suspension was stirred under nitrogen for 2 hr until hydrogen evolution ceased. 1-Bromo-2-chloroethane (6.33 g, 3.77 ml, 0.04425 mol) was added dropwise and the reaction mixture allowed to stir at room temperature under nitrogen overnight. The reaction mixture was poured onto ice-water (800 ml) with stirring for 1 hr, filtered and washed with water (200 ml) to leave a white solid which was dried in vacuo at 50° C. to give a solid. Mp 74–75° C.

Similarly prepared were
Ethyl 1-(2-chloroethyl)-3,4-dihydro-3-(1-methylethyl)-1H-2,1,3-benzothiadiazine-2,2-dioxide-6-carboxylate. (Prepared from ethyl 3,4-dihydro-3-(1-methylethyl)-1H-2,1,3-benzothiadiazine-2,2-dioxide-6-carboxylate)

Mp 96° C.

6-t-Butyldimethylsiloxymethyl-1-(2-chloroethyl)-3,4-dihydro-3-(1-methylethyl)-1H-2,1,3-benzothiadiazine-2,2-dioxide. (Prepared from 6-t-butyldimethylsiloxymethyl-3,4-dihydro-3-(1-methylethyl)-1H-2,1,3-benzothiadiazine-2,2-dioxide)

$^1$H-NMR (CDCl$_3$, 300 Mz), δ: 7.25–7.15 (2H, m), 7.03 (NH, s), 6.92 (1H, d), 4.66 (2H, s), 4.54 (2H, s), 4.16 (1H, h), 4.02 (2H, t), 3.74 (2H, t), 1.13 (6H, 10 d), 0.92 (9H, s), 0.08 (6H, s).

6-Acetyl-1-(2-chloroethyl)-3,4-dihydro-3-(1-methylethyl)-1H-2,1,3-benzothiadiazine-2,2-dioxide. (Prepared from 6-acetyl-3,4-dihydro-3-(1-methylethyl)-1H-2,1,3-benzothiadiazine-2,2-dioxide)

δ($^1$H NMR, CDCl$_3$, ppm): 0.9 (6H, d), 2.60 (3H, s), 3.65 (2H, t), 3.90 (1H, m), 4.00 (2H, t) 4.60 (2H, s), 7.00 (1H, d), 7.70 (2H, m).

1-(2-Chloroethyl)-3,4-dihydro-6-(ethylsulfonyl)-3-(1-methylethyl)-1H-2,1,3-benzothiadiazine-2,2-dioxide. (Prepared from 3,4-dihydro-6-(ethylsulfonyl)-3-(1-methylethyl)-1H-2,1,3-benzothiadiazine-2,2-dioxide)

δ($^1$H NMR, DMSO, ppm): 1.00 (9H, m), 3.10 (2H, q), 3.70 (2H, t), 3.90 (1H, m), 4.10 (2H, t), 4.70 (2H, s), 7.20 (1H, d), 7.60 (2H, m).

1-(2-Chloroethyl)-3,4-dihydro-3-(1-methylethyl)-7-(methylthio)-1H-2,1,3-benzothiadiazine-2,2-dioxide. (Prepared from 3,4-dihydro-3-(1-methylethyl)-7-(methylthio)-1H-2,1,3-benzothiadiazine-2,2-dioxide).

δ($^1$H NMR, DMSO, ppm): 1.20 (6H, d), 2.50 (3H, s), 3.80 (2H, t), 4.1 (3H, m), 4.55 (2H, s), 6.9 (3H, m).

1-(2-Chloroethyl)-3,4-dihydro-3-(1-methylethyl)-1H-2,1,3-benzothiadiazine-2,2-dioxide-6-carboxamide.

Ethyl 1-(2-chloroethyl)-3,4-dihydro-3-(1-methylethyl)-1H-2,1,3-benzothiadiazine-2,2-dioxide-6-carboxylate (3.96 g, 0.01327mol) was dissolved in dry DMF (20 ml) and to this solution, with stirring, was added 60% sodium hydride oil dispersion (0.6 g, 0.0158 mol) in portions. This solution was stirred for 30 mins then cooled to 0–5° C. in an ice-bath. To this solution was added 1-bromo-2-chloroethane (2.42 ml, 0.029 mol) and the temperature was raised to 60° C. and maintained for 24 hrs. The solution was quenched in water, extracted with ethyl acetate (2×) and the organic phase washed with water, brine and dried over magnesium sulphate. After filtering and removal of the solvent, the residue was triturated with hexane, filtered and dried. (4.11 g; 86% yield) The above material (2.9 g, 0.008 mol) was dissolved in THF (50 ml) and lithium hydroxide solution (12 ml, 0.024 mol) added. The stirred solution was heated under gentle reflux for 17 hrs and then, after removal of the solvent, the residue was dissolved in water and extracted with chloroform. After filtration through Celite®, the aqueous phase was acidified with 2N HCl (15 ml; 0.03 mol). A white precipitate was filtered off, washed with water and dried. (2.48 g, 93% yield). The above carboxylic acid (1.16 g, 0.0035 mol) was suspended in hexane (50 ml) and to this was added thionyl chloride (3.0 ml, 0.035 mol) and 2 drops of pyridine. The mixture was heated under reflux for 1 hr and then evaporated to dryness, azeotroping with hexane. The product was dissolved in dry THF (30 ml) and ammonia (0.88 g/ml) added slowly until basic. After stirring for 30 mins the solution was evaporated to near dryness and partitioned between ethyl acetate and water. The organic phase was washed with water and brine, dried (MgSO$_4$), filtered and the solvent removed to produce a gum which on triturating with ether gave a solid, 1-(2-chloroethyl)-3,4-dihydro-3-(1-methylethyl)-1H-2,1,3-benzothiadiazine-2,2-dioxide-6-carboxamide. Mp 137° C.

Similarly prepared was
1-(2-Chloroethyl)-3,4-dihydro-3-(1-methylethyl)-1H-2,1,3-benzothiadiazine-2,2-dioxide-6-N-methylcarboxamide. (Prepared from ethyl 1-(2-chloroethyl)-3,4-dihydro-3-(1-methylethyl)-1H-2,1,3-benzothiadiazine-2,2-dioxide-6-carboxylate).

δ($^1$H NMR, CDCl$_3$, ppm) 7.6 (2H, m), 7.0 (1H, m), 6.1 (1H, NH), 4.1 (3H, m), 3.8 (2H, t), 3.0 (3H, db), 1.1 (6H, d).

1-(2-Chloroethyl)-3,4-dihydro-3-(1-methylethyl)-6-methysulfinyl-1H-2,1,3-benzothiadiazine-2,2-dioxide.

3,4-Dihydro-3-(1-methylethyl)-6-methythio-1H-2,1,3-benzothiadiazine-2,2-dioxide (10 g, 0.0299 mol) was dissolved in glacial acetic acid (100 ml) and sodium perborate (4.6 g, 0.0299 mol) added. The suspension was allowed to stir at room temperature under nitrogen for 18 hr and then was poured into water (500 ml) and extracted with ethyl acetate (2×500 ml). The organic phase was washed with water (2×500 ml), saturated sodium hydrogen carbonate solution (500 ml), dried (MgSO4), filtered and evaporated under reduced pressure to leave a pale yellow oil. After flash chromatography (eluting with ethyl acetate-hexane, then ethyl acetate), the product after removal of solvent crystallised on standing to give a solid.

δ($^1$H NMR, CDCl$_3$, ppm): 7.5 (2H, m), 7.0 (1H, d), 4.6 (2H, m), 4.2 (1H, m), 4.1 (2H, t), 2.7 (3H, s), 1.1 (6H, m).

Similarly prepared was
1-(2-Chloroethyl)-3-cyclopropylmethyl-6-methylsulphinyl-3,4-dihydro-1H-2,1,3-benzothiadiazine-2,2-dioxide. (Prepared from 3-cyclopropylmethyl-3,4-dihydro-6-methylthio-1H-2,1,3-benzothiadiazine-2,2-dioxide).

δ($^1$H NMR, CDCl$_3$, ppm) 7.4 (2H, m), 6.9 (1H, db), 4.6 (2H, s), 4.0 (2H, t), 3.6 (2H, t), 2.7 (2H, m), 2.5 (3H, s), 0.8 (1H, m), 0.4 (2H, m), 0.0 (2H, m).

1-(2-Chloroethyl)-3,3-dimethyl-6-methylthio-2(1H)-quinolinone.

Methanesulfonyl chloride (1.05 ml, 1.56 g, 0.014 mol) was added to a solution of 3,4-dihydro-3,3-dimethyl-1-(2-hydroxyethyl)-6-methylthio-2(1H)-quinolinone (2.88 g, 0.011 mol) and triethylamine (2.27 ml, 1.64 g, 0.016 mol) in dichloromethane (50 ml) at 0° C. under nitrogen and the resultant mixture was stirred for 20 mins. Then the mixture was allowed to warm to room temperature and sirred for 20 hr. The reaction mixture was then washed with water (2×20 ml), dried (MgSO$_4$), filtered and concentrated in vacuo. The residue was then dissolved in carbon tetrachloride (30 ml), filtered and the solvent was evaporated in vacuo to afford 1-(2-chloroethyl)-3,3-dimethyl-6-methylthio-2(1H)-quinolinone as an oil which solidified on standing.

δ($^1$H NMR, CDCl$_3$, ppm): 7.3 (1H, dd), 7.2 (1H, d), 7.1 (1H, d), 4.4 (2H, t), 3.8 (2H, t), 2.9 (2H, s) , 2.6 (3H, s), 1.3 (6H, s).

1-(2-Chloroethyl)-3,4-dihydro-3-(1-methylethyl)-6-methysulfonyl-1H-2,1,3-benzothiadiazine-2,2-dioxide.

A 500 mL 3 necked flask equipped thermometer, pressure equalized dropping funnel, nitrogen bubbler and magnetic stirrer bar was charged with 1-(2-chloroethyl)-3,4-dihydro-3-(1-methylethyl)-6-methylthio-1H-2,1,3-benzothiadiazine-2,2-dioxide (10.0 g, 0.0299 mol) and chloroform (200 ml). To this solution was added in one portion m-chloroperbenzoic acid (20.6 g , ~4 equivalents, nominal purity 56–86%), this resulted in an exotherm which raised the temperature from 20° C. to 50° C. This solution was then stirred for 15 mins, water (100 ml) was added then 2M sodium hydroxide (100 ml). The organic layer was separated, washed again with 2M sodium hydroxide (100 ml), then water (100 ml) dried (MgSO$_4$), filtered and the filtrate evaporated under reduced pressure to leave a white-cream foam, which was dried at 45° C. in vacuo to yield the product.

δ($^1$H NMR, CDCl$_3$, ppm): 7.8 (1H, d), 7.7 (1H, s), 7.1 (1H, d), 4.7 (2H, s), 4.2 (1H, m), 4.2 (2H, t), 3.0 (3H, s), 1.1 (6H, d)

Similarly prepared were 1-(2-Chloroethyl)-3,4-dihydro-3-(1-methylethyl)-7-(methylsulfonyl)-1H-2,1,3-benzothiadiazine-2,2-dioxide. (Prepared from 1-(2-chloroethyl)-3,4-dihydro-3-(1-methylethyl)-7-(methylthio)-1H-2,1,3-benzothiadiazine-2,2-dioxide.

MW=366 [M+H$^+$=367]

1-(2-Chloroethyl)-3,4-dihydro-3,3-dimethyl-6-methylsulfonyl-2(1H)-quinolinone. (Prepared from 1-(2-chloroethyl)-3,4-dihydro-3,3-dimethyl-6-methylthio-2(1H)-quinolinone.

δ($^1$H NMR, CDCl$_3$, ppm): 7.8 (1H, dd), 7.7 (1H, d), 7.1 (1H, d), 4.2 (2H, t), 3.6 (2H, t), 3.0 (3H, s), 2.8 (2H, s), 1.1 (6H, s).

1-(2-Chloroethyl)-1,3-dihydro-3,3-dimethyl-5-methylsulfinyl-2H-indol-2-one.

5-Bromo-3,3-dimethyl-1,3-dihydro-2H-indol-2-one (3.4 g, 0.0142 mol) was dissolved in freshly distilled tetrahydrofuran and cooled to −75° C. under nitrogen. n-Butyllithium in hexane (2.5M, 15 ml, 0.0375 mol) was added and the mixture was stirred at −70° C. for 1 hour. Dimethyl disulfide (2 ml, 1.692 g, 0.0272 mol) was added and the mixture allowed to warm to room temperature. Aqueous ammonium chloride was added and the mixture was concentrated under reduced pressure, the resulting oil was taken up in ethyl acetate and dried (MgSO$_4$), filtered and concentrated under reduced pressure to give a white solid (3.5 g) This solid was dissolved in dimethylformamide and sodium hydride (0.6 g) was added and the mixture stirred for 20 mins at room temperature before 1-bromo-2-chloroethane (2.5 g, 0.0174 mol) was added and then the mixture warmed to 60° C. overnight. The reaction mixture was poured into aqueous ammonium chloride solution, extracted with ethyl acetate washed with water and dried. The solvent was reduced in vacuo and the resultant solution filtered through a silica pad to give an oil (4 g). This oil was dissolved in dichloromethane and m-chloroperbenzoic acid added portionwise. The reaction mixture in dichloromethane was then washed with sodium hydrogen carbonate solution, the dichloromethane solution dried, evaporated in vacuo and the residue chromatographed on silica eluting with ethyl acetate/hexane (3:2), then ethyl acetate/methanol (7:1) to give 1-(2-chloroethyl)-1,3-dihydro-3,3-dimethyl-5-methylsulfinyl-2H-indol-2-one. $^1$H NMR (300 MHz, CDCl$_3$) δ7.8, d (1H), 7.5, d d (1H), 7.0, d (1H), 4.1, t, (2H), 3.8, t, (2H), 2.8, s, (3H), 1.4, s, (6H).

Similarly prepared was 1-(2-Chloroethyl)-1,3-dihydro-3,3-dimethyl-5-methylsulfonyl-2H-indol-2-one (Prepared from 5-Bromo-3,3-dimethyl-1,3-dihydro-2H-indol-2-one as for the synthesis of 1-(2-chloroethyl)-1,3-dihydro-3,3-dimethyl-5-methylsulfinyl-2H-indol-2-one but with the addition of excess of m-chloroperbenzoic acid).

$^1$H NMR (300 MHz, CDCl$_3$) δ7.9, d db , (1H), 7.8, d (1H), 7.1, d d (1H), 4.1, m, (2H), 3.8, m, (2H), 3.0, (3H), 1.4, s, (6H).

2-Oxo-oxazolidine-3-sulfonic acid isopropyl-amide

To a 250 L glass lined reactor initially charged with dichloromethane (42 L) was added chlorosulfonyl isocyanate (4.5 kg, 31.8 moles) at room temperature and under a nitrogen atmosphere.

The reaction mixture was cooled to about 1° C. and a solution of 2-bromoethanol (4.00 kg, 1 eq.) in dichloromethane (14 L) was slowly added over 51 minutes in order to keep the reaction temperature between 0 and 10° C. Stirring of the reaction mixture was continued at the same temperature for a minimum of 30 minutes. Progress of the reaction was monitored by $^1$H-NMR. A mixture of isopropylamine (2.1 kg, 1.1 eq.) and triethylamine (7.1 kg) in dichloromethane (28 L) was then added at such an addition rate that the reaction temperature was maintained between 0 and 10° C. The solution was heated up to room temperature. Aqueous hydrochloric acid (~0.2 N, 28.5 kg) was then added and the pH of the reaction mixture was adjusted to about 2 by addition of concentrated hydrochloric acid (450 ml in 2 portions). The reaction mixture was decanted and the separated organic layer washed with aqueous hydrochloric acid (28.1 kg, ~0.05 N). The decanted and separated organic layer was washed with water (28 kg). To the decanted and separated organic layer, water (28 kg) was then added, and the reactor was placed under vacuum to distil the maximum of dichloromethane while controlling the temperature below 25° C. (84.4 kg of distillate). The resulting suspension was stirred for a minimum of 2 hours at room temperature, filtrated, rinsed twice wish water (2×7 L) and dried under vacuum at about 50° C. during 16 hours to afford the 2-oxo-oxazolidine-3-sulfonic acid isopropyl-amide.

1-Methylethylamino-1-sulfonic acid (4-methanesulfonylphenyl)-amide

A 100 L glass lined reactor was charged with acetonitrile (17.8 kg) and 4-methylsulfonylaniline hydrochloride (3.36 kg, 16.2 moles) under stirring at room temperature. Triethylamine (4.5 kg) and 2-oxo-oxazolidine-3-sulfonic acid isopropyl-amide (3.70 kg, 1.1 eq.) were then added at the same temperature. The reaction mixture was heated to reflux and stirred at the same temperature for a minimum of 6 hours. The solution was then slowly cooled to room temperature and kept agitated over night. Water was slowly added over 40 minutes and the reactor was placed under vacuum to distil as much as possible of acetonitrile (27.8 kg of distillate) while maintaining the reaction temperature below 40° C. The suspension was cooled to room temperature and stirred for a minimum of 2 hours before filtering the product. The cake was rinsed with water (16.2 kg) and dried under vacuum at about 50° C. for a minimum of 16 hours to yield the 1-methylethylamino-1-sulfonic acid (4-methanesulfonylphenyl)-amide.

EXAMPLES 1 TO 5

1-[2-[4-(6-Fluoro-1H-indol-3-yl)-3,6-dihydro-1(2H)-pyridinyl]ethyl]-3,4-dihydro-3,3-dimethyl-6-methylsulfonyl-2(1H)-quinolinone.

1-(2-Chloroethyl)-3,4-dihydro-3,3-dimethyl-6-methylsulfonyl-2(1H)-quinolinone (1.0 g, 0.0032 mol), 6-fluoro-3-(1,2,3,6-tetrahydro-4-pyridinyl)-1H-indole (0.684 g, 0.0032 mol), sodium iodide (0.15 g, 0.001 mol) and potassium carbonate (1.38 g, 0.010 mol) were suspended in acetonitrile (45 ml). The reaction mixture was heated at reflux under nitrogen for 20 hr. The product mixture was then cooled to room temperature. The solvent was evaporated in vacuo. The residue was dissolved in ethyl acetate (50 ml) and washed with water (50 ml). The organic layer was then dried (MgSO$_4$), filtered and concentrated in vacuo. The residue was chromatographed to afford 1-[2-[4-

(6-fluoro-1H-indol-3-yl)-3,6-dihydro-1(2H)-pyridinyl] ethyl]-3,4-dihydro-3,3-dimethyl-6-methylsulfonyl-2(1H)-quinolinone as a yellow foam. δ($^1$H NMR, DMSO, ppm): 1.28 (6H, s), 2.68 (2H, m), 3.14 (2H, s), 3.40 (3H, s), 3.55 (3H, br), 3.96 (1H, br), 4.06 (1H, br), 4.30 (1H, d), 4.60 (2H, t), 6.36 (1H, s), 7.11 (1H, dt), 7.35 (1H, dd), 7.78 (2H, m), 8.00 (3H, m), 11.56 (1H, s).

Similarly prepared were
1-[2-[4-(6-Fluoro-1H-indol-3-yl)-3,6-dihydro-1(2H)-pyridinyl]ethyl]-3,3-dimethyl-5-methylsulfinyl-1,3-dihydro-2H-indol-2-one. Mp 46–48° C.

1-[2-[4-(6,7-Difluoroindol-3-yl)- 3,6-dihydro-1(2H)-pyridinyl]ethyl]-3,3-dimethyl-5-methylsulfinyl-1,3-dihydro-2H-indol-2-one. Mp 173.5–175.5° C.

1-[2-[4-(6-Fluoro-1H-indol-3-yl)-3,6-dihydro-1(2H)-pyridinyl]ethyl]-3,3-dimethyl-5-methylsulfonyl-1,3-dihydro-2H-indol-2-one. Mp 95–98° C.

1-[2-[4-(6,7-Difluoro-1H-indol-3-yl)-3,6-dihydro-1(2H)-pyridinyl]ethyl]-3,3-dimethyl-5-methylsulfonyl-1,3-dihydro-2H-indol-2-one.
Mp 222–223° C.

EXAMPLES 6 TO 22

3,4-Dihydro-6-ethylsulfonyl-1-[2-[4-(6-fluoro-1H-indol-3-yl)-3,6-dihydro-1(2H)-pyridinyl]ethyl]-3-(1-methylethyl)-1H-2,1,3-benzothiadiazine-2,2-dioxide.

1-(2-Chloroethyl)-3,4-dihydro-6-(ethylsulfonyl)-3-(1-methylethyl)-1H-2,1,3-benzothiadiazine-2,2-dioxide (1.03 g, 0.0027 mol), 6-fluoro-3-(1,2,3,6-tetrahydro-4-pyridinyl)-1H-indole (0.706 g, 0.0033 mol), sodium iodide (0.408 g, 0.0027 mol) and sodium bicarbonate (1.586 g, 0.015 mol) were suspended in water (75 ml). The reaction mixture was heated at reflux overnight. The product mixture was then cooled to room temperature. The product was extracted into ethyl acetate (3×50 ml). The organic extracts were combined, washed with water (150 ml), dried (MgSO$_4$) and concentrated in vacuo to afford 3,4-dihydro-6-ethylsulfonyl-1-[2-[4-(6-fluoro-1H-indol-3-yl)-3,6-dihydro-1(2H)-pyridinyl]ethyl]-3-(1-methylethyl)-1H-2,1,3-benzothiadiazine-2,2-dioxide. δ($^1$H NMR, DMSO, ppm): 1.10 (9H, m), 2.50 (2H, m), 2.80 (4H, m), 3.25 (4H, m), 4.10 (3H, m), 4.90 (2H, s), 6.10 (1H, s), 6.90 (1H, dt), 7.20 (1H, dd), 7.35 (1H, d), 7.40 (1H, d), 7.80 (3H, m), 11.20 (1H, s).

Similarly prepared were
6-Carboxamido-3,4-dihydro-1-[2-[4-(6-fluoro-1H-indol-3-yl)-3,6-dihydro-1(2H)-pyridinyl]ethyl]-3-(1-methylethyl)-1H-2,1,3-benzothiadiazine-2,2-dioxide.
Mp 142° C.

3,4-Dihydro-1-[2-[4-(6-fluoro-1H-indol-3-yl)-3,6-dihydro-1(2H)-pyridinyl]ethyl]-6-N-methylcarboxamido-3-(1-methylethyl)-1H-2,1,3-benzothiadiazine-2,2-dioxide.
δ($^1$H NMR, DMSO, ppm): 8.3 (1H, m), 7.7 (3H, m), 7.4 (1H, m), 7.3 (2H, db), 6.9 (1H, d db), 6.1 (1H, m), 4.7 (2H, s), 4.0 (3H, m), 3.3 (4H, m), 2.8 (7H, m), 1.0 (6H, db).

1-[2-[4-(6,7-Difluoro-1H-indol-3-yl)-1-piperidinyl]ethyl]-3,4-dihydro-3-(1-methylethyl)-6-methylsulfinyl-1H-2,1,3-benzothiadiazine-2,2-dioxide.
Mp 198.6–200.8° C.

1-[2-[4-(1H-Indol-3-yl)-3,6-dihydro-1(2H)-pyridinyl] ethyl]-3,4-dihydro-3-(1-methylethyl)-6-methylsulfinyl-1H-2,1,3-benzothiadiazine-2,2-dioxide.
δ($^1$H NMR, DMSO, ppm): 7.9 (1H, m), 7.7 (2H, m), 7.5 (2H, s), 7.4 (1H, m), 7.2 (3H, m), 6.2 (1H, m), 4.9 (2H, s), 4.1 (3H, m), 3.4 (4H, m) 2.7 (7H, m), 1.2 (6H, d).

6-Acetyl-3,4-dihydro-1-[2-[4-(6-fluoro-1H-indol-3-yl)-3,6-dihydro-1(2H)-pyridinyl]ethyl]-3-(1-methylethyl)-1H-2,1,3-benzothiadiazine-2,2-dioxide.
Mp 80–86° C.

1-[2-[4-(6-Fluoro-1H-indol-3-yl)-3,6-dihydro-1(2H)-pyridinyl]ethyl]-3,4-dihydro-3-(1-methylethyl)-6-methylsulfonyl-1H-2,1,3-benzothiadiazine-2,2-dioxide.
Mp 118–120° C.

1-[2-[4-(6-Fluoro-1H-indol-3-yl)-3,6-dihydro-1(2H)-pyridinyl]ethyl]-3,4-dihydro-3-(1-methylethyl)-6-methylsulfinyl-1H-2,1,3-benzothiadiazine-2,2-dioxide.
Mp 105–107° C.

1-[2-[4-(6-Fluoro-1H-indol-3-yl)-3,6-dihydro-1(2H)-pyridinyl]ethyl]-3,4-dihydro-3-(1-methylethyl)-6-methylthio-1H-2,1,3-benzothiadiazine-2,2-dioxide.
Mp 80–8° C.

1-[2-[4-(6-Fluoro-1H-indol-3-yl)-3,6-dihydro-1(2H)-pyridinyl]ethyl]-3,4-dihydro-3-(1-cyclopropylmethyl)-6-methylsulfinyl-1H-2,1,3-benzothiadiazine-2,2-dioxide.
Mp 134° C.

1-[2-[4-(5-Fluoro-1H-indol-3-yl)-3,6-dihydro-1(2H)-pyridinyl]ethyl]-3,4-dihydro-3-(1-methylethyl)-6-methylsulfinyl-1H-2,1,3-benzothiadiazine-2,2-dioxide.
δ($^1$H NMR, DMSO, ppm) 7.6 (2H, m), 7.5 (1H, dd), 7.4 (1H, s), 7.3 (1H, q), 7.2 (2H, d), 6.9 (1H, m), 6.0 (1H, m), 4.8 (2H, s), 4.0 (3H, m), 3.2 (4H, m), 2.7 (7H, m), 1.0 (6H, m)

1-[2-[4-(6-Fluoro-1H-indol-3-yl)-1-piperidinyl]ethyl]-3,4-dihydro-3-(1-methylethyl)-6-methylsulfinyl-1H-2,1,3-benzothiadiazine-2,2-dioxide.
δ($^1$H NMR, DMSO, ppm): 7.5 (2H, m), 7.4 (1H, m), 7.2 (1H, s), 7.1 (1H, m), 7.0 (1H, s), 6.7 (1H, m), 4.6 (2H, s), 4.0 (1H, m), 3.8 (2H, t), 2.8 (3H, s), 2.9 (2H, m), 2.5 (2H, t), 2.1 (2H, t), 1.8 (2H, m), 1.6 (2H, m), 1.0 (6H, d).

1-[2-[4-(6-Fluoro-1H-indol-3-yl)-3,6-dihydro-1(2H)-pyridinyl]ethyl]-3,4-dihydro-3-(1-cyclopropylmethyl)-6-methylsulfonyl-1H-2,1,3-benzothiadiazine-2,2-dioxide.
δ($^1$H NMR, DMSO, ppm): 7.7 (3H, m), 7.2 (2H, m), 7.0 (1H, dd), 6.7 (1H, m), 6.0 (1H, m), 4.0 (2H, m), 3.2 (2H, m), 3.0 (6H, m), 2.7 (2H, d) 2.5 (3H, m), 0.9 (1H, m), 0.3 (2H, m), 0.0 (2H, m).

1-[2-[4-(6,7-Difluoro-1H-indol-3-yl)-3,6-dihydro-1(2H)-pyridinyl]ethyl]-3,4-dihydro-3-(1-cyclopropylmethyl)-6-methylsulfonyl-1H-2,1,3-benzothiadiazine-2,2-dioxide.
δ($^1$H NMR, DMSO, ppm): 7.7 (3H, m), 7.4 (1H, dd), 7.3 (1H, m), 7.2 (1H, d), 6.9 (1H, m), 6.0 (1H, m), 4.8 (2H, s), 4.0 (2H, m), 3.2 (2H, m), 3.0 (6H, m), 2.7 (2H, d), 2.5 (2H, m), 0.9 (1H, m), 0.3 (2H, m), 0.0 (2H, m).

1-[2-[4-(6-Fluoro-1H-indol-3-yl)-3,6-dihydro-1(2H)-pyridinyl]ethyl]-3,4-dihydro-3-(1-methylethyl)-7-methylsulfonyl-1H-2,1,3-benzothiadiazine-2,2-dioxide.
δ($^1$H NMR, DMSO, ppm): 7.6 (1H, m), 7.5 (2H, m), 7.4 (1H, d), 7.2 (1H, m), 7.0 (1H, dd), 6.8 (1H, m), 6.0 (1H, m), 4.6 (2H, s), 3.9 (3H, m), 3.1 (7H, m), 2.8 (4H, d), 1.0 (6H, d).

1-[2-[4-(6,7-Difluoro-1H-indol-3-yl)-3,6-dihydro-1(2H)-pyridinyl]ethyl]-3,4-dihydro-3-(1-methylethyl)-6-methylsulfonyl-1H-2,1,3-benzothiadiazine-2,2-dioxide.
δ($^1$H NMR, DMSO, ppm): 7.8 (2H, m), 7.6 (1H, m), 7.5 (1H, m), 7.3 (1H, d), 7.0 (1H, dd), 6.1 (1H, m), 4.8 (2H, s), 4.0 (3H, m), 3.3 (2H, m), 3.2 (6H, m), 2.7 (3H, m), 1.0 (6H, d).

1-[2-[4-(6-Fluoro-1H-indol-3-yl)-3,6-dihydro-1(2H)-pyridinyl]ethyl]-6-t-butyldimethylsiloxymethyl-3,4-dihydro-3-(1-methylethyl)-1H-2,1,3-benzothiadiazine-2,2-dioxide.
$^1$H-NMR (CDCl$_3$, 300 Mz), δ: 8.15 (broad s, NH), 7.76 (dd, 1H), 7.20–6.84 (m, 6H), 6.14 (broad s, 1H), 4.65 (s, 2H), 4.57 (s, 2H), 4.13 (h, 1H), 3.98 (t, 2H), 3.30 (broad s, 2H), 2.87-2.79 (m, 4H), 2.58 (broad s, 2H), 1.10 (d, 6H), 0.90 (s, 9H), 0.09 (s, 6H).

EXAMPLE 23
1-[2-[4-(6-Fluoro-1H-indol-3-yl)-3,6-dihydro-1(2H)-pyridinyl]ethyl]-3,4-dihydro-3-(1-methylethyl)-6-methylsulfonyl-1H-2,1,3-benzothiadiazine-2,2-dioxide.

To a stirred solution of 3,4-dihydro-3-(1-methylethyl)-6-methylsulfonyl-1H-2,1,3-benzothiadiazine-2,2-dioxide (0.38 g, 0.00125 mol), triphenylphosphine (0.39 g, 0.0015 mol) and 2-(4-(6-fluoro-1H-indol-3-yl)-3,6-dihydro-1(2H)-pyridinyl)ethanol (0.26 g, 0.0015 mol) in DMF (10 ml) at −5° C. was added dropwise under nitrogen diethyl azodicarboxylate (0.24 ml, 0.0015 mol). The reaction was stirred at −5° C. for 10 mins then allowed to warm to room temperature stirring for a further 20 mins. After the addition of ethyl acetate (30 ml) and water (20 ml), the organic layer was washed with water (4×20 ml) the organics dried (MgSO$_4$) and concentrated in vacuo to afford 0.52 g of 1-[2-[4-(6-fluoro-1H-indol-3-yl)-3,6-dihydro-1(2H)-pyridinyl]ethyl]-3,4-dihydro-3-(1-methylethyl)-6-methylsulfonyl-1H-2,1,3-benzothiadiazine-2,2-dioxide as a yellow solid. Mp 118–120° C.

EXAMPLE 24
1-[2-[4-(6-Fluoro-1H-indol-3-yl)-3,6-dihydro-1(2H)-pyridinyl]ethyl]-3,4-dihydro-6-hydroxymethyl-3-(1-methylethyl)-1H-2,1,3-benzothiadiazine-2,2-dioxide.

Tetrabutylammonium fluoride (2 ml, 0.002 mol, 1M in THF) was added to a suspension of 1-[2-[4-(6-fluoro-1H-indol-3-yl)-3,6-dihydro-1(2H)-pyridinyl]ethyl]-6-t-butyldimethylsiloxymethyl-3,4-dihydro-3-(1-methylethyl)-1H-2,1,3-benzothiadiazine-2,2-dioxide (1.1 g, 0.0018 mol) in THF (18 ml) under argon then stirred at room temperature for 2 h, evaporated to dryness and purified by flash chromatography using dichlormethane/methanol (97:3) as eluent, to give 1-[2-[4-(6-fluoro-1H-indol-3-yl)-3,6-dihydro-1(2H)-pyridinyl]ethyl]-3,4-dihydro-6-hydroxymethyl-3-(1-methylethyl)-1H-2,1,3-benzothiadiazine-2,2-dioxide as a pale yellow solid. Mp: 113–115° C. $^1$H-NMR (CDCl$_3$, 300 Mz), δ: 8.09 (NH, s), 7.76 (1H, dd), 7.22 (1H, d), 7.11 (1H, d), 7.08 (1H, s), 7.01 (1H, dd), 6.98 (1H, d), 6.88 (1H, dt), 6.13 (1H, t), 3.29 (2H, s), 2.85-2.81 (4H, m), 2.58 (2H, s), 1.11 (6H, d).

EXAMPLE 25
1,3-Dihydro-1-[2-[4-(6-fluoro-1H-indol-3-yl)-3,6-dihydro-1(2H)-pyridinyl]ethyl]-3-(1-methylethyl)-5-(methylsulfonyl)-1H-2,1,3-benzothiadiazole-2,2-dioxide.

Sodium triacetoxyborohydride (0.68 g, 0.00319 mol) was added portionwise to (1,3-dihydro-2,2-dioxido-3-methyl-5-methylsulphonyl-2,1,3-benzothiadiazol-1-yl)ethanal (0.97 g, 0.00319 mol) and 6-fluoro-3-(1,2,3,6-tetrahydro-4-pyridinyl)-1H-indole (0.69 g, 0.00319 mol) in dichloroethane (60 ml). To this mixture at room temperature was added portionwise 3 drops of acetic acid and the mixture stirred for 1.5 hr. The solution was then diluted with water (100 ml), neutralised with saturated sodium bicarbonate solution and extracted with ethyl acetate (2×70 ml). The organic extracts were washed with water (3×70 ml), dried (MgSO$_4$) filtered and concentrated in vacuo. Column chromatography on the residue afforded 1,3-dihydro-1-[2-[4-(6-fluoro-1H-indol-3-yl)-3,6-dihydro-1(2H)-pyridinyl]ethyl]-3-(1-methylethyl)-5-(methylsulfonyl)-1H-2,1,3-benzothiadiazole-2,2-dioxide.

$^1$H NMR (300 MHz, DMSO) δ, 7.85, (1H, dd), 7.6 (1H, m), 7.2 (1H, dd), 6.9, (1H, m), 6.2 (1H, m), 4.5 (2H, m), 4.1 (2H, m), 4.0 (1H, m), 3.8 (1H, m), 3.6 (2H, m), 3.4 (3H, s), 3.2 (3H, s), 2.8 (2H, m).

EXAMPLES 26 TO 30
Preparation of 1-[2-[4-(6-fluoro-1H-indol-3-yl)-1-piperidinyl]ethyl]-3,4-dihydro-3-(1-methylethyl)-6-methylsulfonyl-1H-2,1,3-benzothiadiazine-2,2-dioxide.

A vial was charged with a solution of [3,4-dihydro-2,2-dioxido-3-(1-methylethyl)-6-methylsulfonyl-1H-2,1,3-benzothiadiazin-1-yl]ethanal in methanol (0.12M, 0.5 ml) and a solution of 4-(6-fluoro-1H-indol-3-yl)-1-piperidine in acetic acid/methanol (1:4) (0.02M, 1 ml). The vial was capped and swirled at room temperature in air on an orbital shaker (100 rpm) for 1 hour. A solution of sodium cyanoborohydride in methanol (0.1M, 0.5 ml) was then added to the contents of the vial. The vial was recapped and agitation continued as before on the orbital shaker for 72 h. The contents of the vial were then applied to a 500 mg SCX ion exchange column pre-conditioned with methanol. The column was then washed with methanol (3 ml). The column was then treated with 2N ammonia in methanol (2×2.5 ml) to release the basic product. Solvent was then removed in vacuo to yield 1-[2-[4-(6-fluoro-1H-indol-3-yl)-1-piperidinyl]ethyl]-3,4-dihydro-3-(1-methylethyl)-6-methylsulfonyl-1H-2,1,3-benzothiadiazine-2,2-dioxide as a pale yellow gum.

$^1$H NMR (300 MHz, CDCl$_3$) δ7.9 (1H, s), 7.8 (1H, dd), 7.6 (1H, d), 7.5 (1H, dd), 7.1 (1H, d) 7.0 (1H, dd), 6.9 (1H, d), 6.8 (1H, t), 4.7 (2H, s), 4.2 (1H, t), 4.0 (2H, t), 3.1 (2H, d), 3.0 (3H, s), 2.7 (3H, m), 2.3 (2H, t), 1.8 (3H, d), 1.1 (7H, d).

Similarly prepared were
1-[2-[4-(6-Chloro-1H-indol-3-yl)-1-piperidinyl]ethyl]-3,4-dihydro-3-(1-methylethyl)-6-methylsulfonyl-1H-2,1,3-benzothiadiazine-2,2-dioxide.

$^1$H NMR (300 MHz, CDCl$_3$) δ7.9 (1H, s), 7.8 (1H, dd), 7.6 (1H, d), 7.5 (1H, d), 7.3 (1H, d) 7.1 (2H, d), 7.0 (1H, dd), 6.9 (1H, d), 4.7 (2H, s), 4.2 (1H, m), 4.0 (2H, t), 3.1 (2H, d), 3.0 (3H, s), 2.7 (3H, m), 2.3 (2H, t), 2.1 (2H, d), 1.8 (2H, q), 1.1 (6H, d).

1-[2-[4-(6-Chloro-1H-indol-3-yl)-3,6-dihydro-1(2H)-pyridinyl]ethyl]-3,4-dihydro-3-(1-methylethyl)-6-methylsulfonyl-1H-2,1,3-benzothiadiazine-2,2-dioxide.

$^1$H NMR (300 MHz, CDCl$_3$) δ8.1 (1H, s), 7.8 (1H, m), 7.7 (1H, d), 7.6 (1H, d), 7.1 (3H, m) 6.1 (1H, m), 4.7 (3H, m), 4.2 (1H, m), 4.1 (2H, t), 3.4 (2H, s), 3.0 (4H, s), 2.8 (4H, m), 2.6 (2H, s), 1.1 (6H, d).

1-[2-[4-(7-Fluoro-1H-indol-3-yl)-3,6-dihydro-1(2H)-pyridinyl]ethyl]-3,4-dihydro-3-(1-methylethyl)-6-methylsulfonyl-1H-2,1,3-benzothiadiazine-2,2-dioxide.

$^1$H NMR (300 MHz, CDCl$_3$) δ8.2 (1H, s), 7.8 (1H, dd), 7.6 (1H, m), 7.2 (2H, m), 7.1 (1H, m), 6.9 (1H, m), 6.2 (1H, m), 4.7 (2H, s), 4.2 (1H, m), 4.1 (2H, t), 3.4 (2H, s), 3.0 (3H, s), 2.8 (4H, m), 2.6 (2H, s), 1.1 (6H, d).

1-[2-[4-(7-Fluoro-1H-indol-3-yl)-1-piperidinyl]ethyl]-3,4-dihydro-3-(1-methylethyl)-6-methylsulfonyl-1H-2,1,3-benzothiadiazine-2,2-dioxide.

$^1$H NMR (300 MHz, CDCl$_3$) δ8.2 (1H, s) , 7.8 (1H, dd), 7.7 (1H, d), 7.4 (1H, d), 7.0 (2H, m), 6.9 (1H, m), 4.7 (2H, s), 4.2 (3H, m), 3.2 (2H, s), 3.0 (3H, s) , 2.8 (2H, s) , 2.6 (1H, s) , 2.4 (2H, s) , 1.3 (4H, s), 1.1 (6H, d).

1-[2-[4-(6,7-Difluoro-1H-indol-3-yl)-1-piperidinyl]ethyl]-3,4-dihydro-3-(1-methylethyl)-6-methylsulfonyl-1H-2,1,3-benzothiadiazine-2,2-dioxide.

$^1$H NMR (300 MHz, CDCl$_3$) δ8.1 (1H, s), 7.8 (1H, dd), 7.7 (1H, d), 7.1 (1H, d), 6.9 (2H, m), 4.7 (2H, s), 4.2 (1H, m), 4.0 (2H, t), 3.1 (2H, d), 3.1 (3H, s), 2.7 (2H, t), 2.3 (2H, t), 2.0 (3H, m), 1.8 (2H, q), 1.1 (6H, d).

1-[2-[4-(6-Fluoro-7-methyl-1H-indol-3-yl)-3,6-dihydro-1(2H)-pyridinyl]ethyl]-3,4-dihydro-3-(1-methylethyl)-6-methylsulfonyl-1H-2,1,3-benzothiadiazine-2,2-dioxide.

$^1$H NMR (300 MHz, CDCl$_3$) δ7.9 (1H, s), 7.8 (1H, dd), 7.6 (2H, m), 7.1 (2H, m), 6.9 (1H, t), 6.1 (1H, s), 4.7 (2H, s), 4.2 (1H, m), 4.1 (2H, t), 3.3 (2H, s), 3.0 (3H, s), 2.8 (2H, t), 2.6 (2H, s), 2.4 (3H, s), 1.1 (6H, d).

The following Examples illustrate typical formulations containing the compound of the invention.

EXAMPLE 31

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 32

Capsules each containing 20 mg of medicament are made as follows:

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatine capsules in 200 mg quantities.

What is claimed is:

1. A compound of the formula:

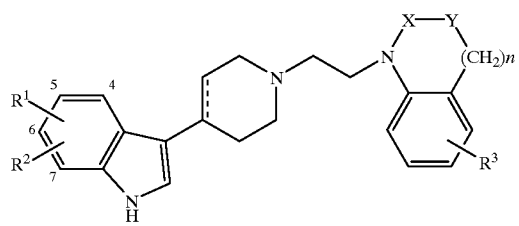

in which $R^1$ and $R^2$ are each hydrogen, halo, cyano or methyl, the dotted line represents an optional double bond,

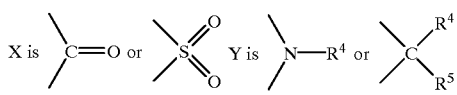

where $R^4$ and $R^5$ are each hydrogen, $C_{1-6}$ alkyl, cyclopropyl or cyclopropyl-$C_{1-6}$ alkyl, n is 0 or 1, and $R^3$ is —$SR^6$, —$SOR^6$, —$SO_2R^6$, —$COR^6$, —$CH_2OH$ or —$CONHR^7$, where $R^6$ is $C_{1-6}$ alkyl and $R^7$ is hydrogen or $C_{1-6}$ alkyl;

provided that when one of $R^1$ and $R^2$ is hydrogen and the other is fluoro,

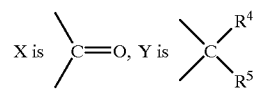

$R^4$ and $R^5$ are each hydrogen or $C_{1-6}$ alkyl, and n is 0, then $R^3$ is not —$COR^6$ or —$CONHR^7$;

or a salt thereof.

2. A compound according to claim 1, of the formula:

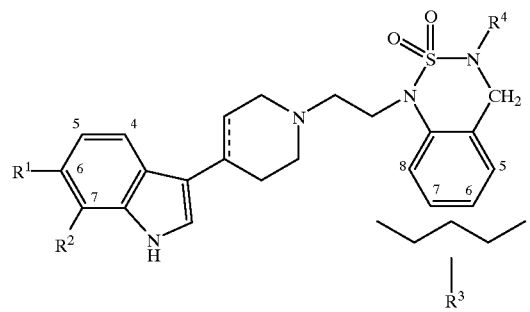

in which $R^1$ and $R^2$ are each hydrogen or fluoro, $R^3$ is at the 6- or 7- position and is —$SOR^6$, —$SO_2R^6$ or —$COR^6$, where $R^4$ and $R^6$ are each $C_{1-6}$ alkyl.

3. A compound according to claim 2 in which $R^1$ is fluoro, $R^2$ is hydrogen, $R^3$ is at the 6-position, $R^4$ is $C_{1-6}$ alkyl, $R^6$ is methyl, and the dotted bond represents a double bond.

4. A compound of the formula:

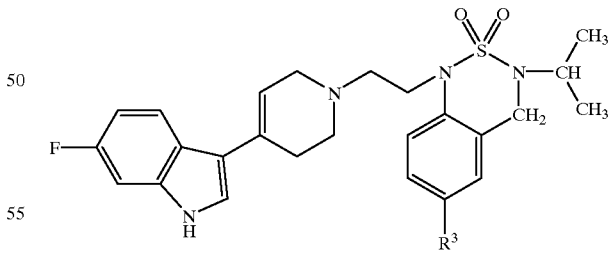

where $R^3$ is —$SOCH_3$ or —$SO_2CH_3$, or a pharmaceutically acceptable salt thereof.

5. A method treating a disorder of the central nervous system selected from the group consisting of depression, anxiety, and schizophrenia which comprises administering an effective amount of a compound according to claim 1, or a pharmaceutically acceptable salt thereof.

6. A compound of the formula:

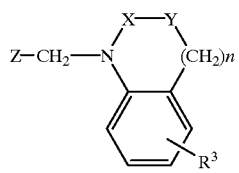

where n is 1, X and Y have the values given in claim 1, and in which Z is (i) —CH$_2$W, where W is a leaving group, or (ii) Z is —CHO; or a salt thereof.

7. A pharmaceutical formulation comprising a compound according to claim 1, or a pharmaceutically acceptable salt thereof, and a pharmaceutically acceptable diluent or carrier therefor.

8. A pharmaceutical formulation comprising a compound according to claim 4, or a pharmaceutically acceptable salt thereof, and a pharmaceutically acceptable diluent or carrier therefor.

9. A method as claimed in claim 5 wherein the disorder is depression or anxiety.

10. A method as claimed in claim 9 wherein the disorder is depression.

* * * * *